US011471451B2

(12) United States Patent
Jain

(10) Patent No.: US 11,471,451 B2
(45) Date of Patent: Oct. 18, 2022

(54) USES OF CRENOLANIB

(71) Applicant: Arog Pharmaceuticals, Inc., Dallas, TX (US)

(72) Inventor: Vinay K. Jain, Dallas, TX (US)

(73) Assignee: AROG PHARMACEUTICALS, INC., Plano, TX (US)

(*) Notice: Subject to any disclaimer, the term of this patent is extended or adjusted under 35 U.S.C. 154(b) by 0 days.

(21) Appl. No.: 16/738,108

(22) Filed: Jan. 9, 2020

(65) Prior Publication Data
US 2021/0052571 A1    Feb. 25, 2021

Related U.S. Application Data

(60) Provisional application No. 62/888,717, filed on Aug. 19, 2019.

(51) Int. Cl.
A61K 31/4709   (2006.01)
C12Q 1/6886    (2018.01)
A61K 31/7068   (2006.01)
A61K 31/7048   (2006.01)
A61K 31/7076   (2006.01)
A61K 45/06     (2006.01)
A61K 31/704    (2006.01)

(52) U.S. Cl.
CPC ........ A61K 31/4709 (2013.01); A61K 31/704 (2013.01); A61K 31/7048 (2013.01); A61K 31/7068 (2013.01); A61K 31/7076 (2013.01); A61K 45/06 (2013.01); C12Q 1/6886 (2013.01); C12Q 2600/156 (2013.01)

(58) Field of Classification Search
CPC ............ A61K 31/4709; A61K 31/7068; A61K 31/7048; A61K 31/7076; A61K 45/06; A61K 31/704; C12Q 1/6886; C12Q 2600/156
USPC ........................................................ 514/34
See application file for complete search history.

(56) References Cited

U.S. PATENT DOCUMENTS

| 5,990,146 A | 11/1999 | Boschelli et al. |
| 7,183,414 B2 | 2/2007 | Tom et al. |
| 2005/0124599 A1 | 6/2005 | Kath et al. |
| 2018/0087114 A1 | 3/2018 | Melnikova et al. |
| 2018/0117031 A1 | 5/2018 | Jain |

FOREIGN PATENT DOCUMENTS

| WO | 1999/016755 | 4/1999 |
| WO | 2001/040217 A1 | 6/2001 |

OTHER PUBLICATIONS

Galanis et al. (Blood. 2014;123(1):94-100).*
Lee et al. (European Journal of Haematology; vol. 92, Issue 6, p. 478-484).*
Kiyoi et al. (Blood, vol. 93, No. 9 (May 1), 1999: pp. 3074-3080).*
Schuurhuis et al. (Blood. 2018;131(12):1275-1291).*
Au et al. (Diagnostic Pathology (2016) 11:11, 1-12).*
Xu (Scientific Reports | (2019) 9:11119, 1-8).*
Gianfelici et al. (Hematology, Springer Verlag, 2010, 90 (7), pp. 845-846).*
Anderson, et al. "Handbook of clinical drug data (10th ed.)" (2002). New York; Toronto: McGraw-Hill Medical Pub. Division.
Daver, et al. "Targeting FLT3 mutations in AML: review of current knowledge and evidence" (2019) Leukemia. doi:10.1038/s41375-018-0357-9, Published online: Jan. 16, 2019.
Ding, et al. "Clonal evolution in relapsed acute myeloid leukaemia revealed by whole-genome sequencing" (Published online Jan. 11, 2012) Nature, 481(7382), 506-510. doi:10.1038/nature10738.
Ommen, H. B. "Monitoring minimal residual disease in acute myeloid leukaemia: a review of the current evolving strategies" (2016) Ther Adv Hematol, 7(1), 3-16. doi:10.1177/2040620715614529.
Papaemmanuil, et al. "Genomic Classification and Prognosis in Acute Myeloid Leukemia" (Jun. 9, 2016). N Engl J Med, 374(23), 2209-2221. doi:10.1056/NEJMoa1516192.
Tyner, et al. "Functional genomic landscape of acute myeloid leukaemia" (Oct. 2018). Nature. doi:10.1038/s41586-018-0623-z.
Van Galen, et al. "Single-Cell RNA-Seq Reveals AML Hierarchies Relevant to Disease Progression and Immunity" (2019). Cell, 176(6), 1265-1281 e1224. doi:10.1016/j.cell.2019.01.031.
Altman, et al. "Phase 1 study of quizartinib in combination with induction and consolidation chemotherapy in patients with newly diagnosed acute myeloid leukemia" Am J Hematol, (2018) 93(2), 213-221. doi:10.1002/ajh.24974.
Bergua, et al. (2016). "A prognostic model for survival after salvage treatment with FLAGIda +/- gemtuzumab-ozogamicine in adult patients with refractory/relapsed acute myeloid leukaemia" (2016) Br J Haematol, 174(5), 700-710. doi:10.1111/bjh.14107.

(Continued)

Primary Examiner — Shaojia A Jiang
Assistant Examiner — Michael C Henry
(74) Attorney, Agent, or Firm — Edwin S. Flores; Daniel J. Chalker; Chalker Flores, LLP

(57) ABSTRACT

The present invention includes methods of monitoring measurable residual disease in patients suffering from a proliferative disorder, determining which patients could benefit from treatment or intervention with crenolanib or salt in reducing residual disease and maintaining remission, and administering a therapeutically effective amount of crenolanib as a single agent or sequentially or concomitantly with another therapeutic agent.

31 Claims, 8 Drawing Sheets

(56) References Cited

OTHER PUBLICATIONS

Cheson, et al. "Reporting Standards for Therapeutic Trials in Acute Myeloid" (Dec. 15, 2003). Revised recommendations of the International Working Group for Diagnosis, Standardization of Response Criteria, Treatment Outcomes, and Reporting Standards for Therapeutic Trials in Acute Myeloid Leukemia. J Clin Oncol, 21(24), 4642-4649. doi:10.1200/JCO.2003.04.036.

Cortes, et al. "Quizartinib, an FLT3 inhibitor, as monotherapy in patients with relapsed or refractory acute myeloid leukaemia: an open-label, multicentre, single-arm, phase 2 trial" Lancet Oncol. (2018) Published online May 30, 2018, doi:10.1016/S1470-2045(18)30240-7.

Cortes, et al. "Quizartinib versus salvage chemotherapy in relapsed or refractory FLT3-ITD acute myeloid leukaemia (QuANTUM-R): a multicentre, randomised, controlled, open-label, phase 3 trial" (2019) Published online Jun. 4, 2019, The Lancet Oncology. doi:10.1016/s1470-2045(19)30150-0.

Fischer, et al. "Phase IIB trial of oral Midostaurin (PKC412), the FMS-like tyrosine kinase 3 receptor (FLT3) and multi-targeted kinase inhibitor, in patients with acute myeloid leukemia and high-risk myelodysplastic syndrome with either wild-type or mutated FLT3" (Oct. 2010). J Clin Oncol, 28(28), 4339-4345. doi:10.1200/JCO.2010.28.9678.

Karanes, et al. A phase III comparison of high dose ARA-C (HIDAC) versus HIDAC plus mitoxantrone in the treatment of first relapsed or refractory acute myeloid leukemia: Southwest Oncology Group Study. Leukemia Research, 23(9), 787-794. doi:https://doi.org/10.1016/S0145-2126(99)00087-9 (1999).

Kohrt, et al. "Second-line mitoxantrone, etoposide, and cytarabine for acute myeloid leukemia: a single-center experience" (2010). Am J Hematol, 85(11), 877-881. doi:10.1002/ajh.21857.

Levis, et al. "In vitro studies of a FLT3 inhibitor combined with chemotherapy: sequence of administration is important to achieve synergistic cytotoxic effects" (Aug. 15, 2004) Blood, 104(4), 1145-1150. doi:10.1182/blood-2004-01-0388.

Levis, et al. "Results from a randomized trial of salvage chemotherapy followed by lestaurtinib for patients with FLT3 mutant AML in first relapse" (Mar. 24, 2011) Blood, 117(12), 3294-3301. doi:10.1182/blood-2010-08-301796.

Meads, et al. "The bone marrow microenvironment as a tumor sanctuary and contributor to drug resistance" (May 1, 2008) Clin Cancer Res, 14(9), 2519-2526. doi:10.1158/1078-0432.CCR-07-2223.

Mort, et al. "Evaluation of cardiomyopathy in acute myeloid leukemia patients treated with anthracyclines" (2019) J Oncol Pharm Pract, 1078155219873014. doi:10.1177/1078155219873014.

Oun, et al. "The side effects of platinum-based chemotherapy drugs: a review for chemists" (May 21, 2018) Dalton Trans, 47(19), 6645-6653. doi:10.1039/c8dt00838h.

Perl, et al. "Gilteritinib or Chemotherapy for Relapsed or Refractory FLT3-Mutated AML" (Oct. 31, 2019) N Engl J Med, 381(18), 1728-1740. doi:10.1056/NEJMoa1902688.

Pratz, et al. "A Phase I Study of Gilteritinib in Combination with Induction and Consolidation Chemotherapy in Patients with Newly Diagnosed AML: Final Results Update" (2021) Paper presented at the EHA. https://library.ehaweb.org/eha/2021/eha2021-virtual-congress/325191/keith.w.pratz.a.phase.1.study.of.gilteritinib.in.combination.with.induction.htmlf=listing%3D3%2Abrowseby%3D8%2Asortby%3D1%2Amedia%3D1 (Abstract Only).

Pratz, et al. "Preliminary Results from a Phase 1 Study of Gilteritinib in Combination with Induction and Consolidation Chemotherapy in Subjects with Newly Diagnosed Acute Myeloid Leukemia (AML)" (2017) Paper presented at the ASH. (Abstract Only).

Pratz, et al. "Updated Results From a PhI Study of Gilteritinib in Combination with Induction and Consolidation Chemotherapyiln Patients with Newly Diagnosed AML" (2019). Paper presented at the EHA.

Rucker, et al. "Molecular landscape and prognostic impact of FLT3-ITD insertion site in acute myeloid leukemia: RATIFY study results" (2021) Leukemia. doi:10.1038/s41375-021-01323-0.

Schlenk, et al. "QuANTUM-First: phase 3, double-blind, placebo-controlled study of quizartinib in combination with induction and consolidation chemotherapy, and as maintenance therapy in patients (pts) with newly diagnosed (NDx) FLT3-ITD acute myeloid leukemia (AML)" (2017) Paper presented at the ESMO. (Abstract Only).

Schlenk, et al. German-Austrian, A. M. L. S. G. (2014). "Differential impact of allelic ratio and insertion site in FLT3-ITD-positive AML with respect to allogeneic transplantation" (Nov. 27, 2014). Blood, 124(23), 3441-3449. doi:10.1182/blood-2014-05-578070.

Sexauer, et al. "Terminal myeloid differentiation in vivo is induced by FLT3 inhibition in FLT3/ITD AML" (Nov. 15, 2012). Blood, 120(20), 4205-4214. doi:10.1182/blood-2012-01-402545.

Stam, et al. "D-HPLC analysis of the entire FLT3 gene in MLL rearranged and hyperdiploid acute lymphoblastic leukemia" (2007) Haematologica, 92(11), 1565-1568. doi:10.3324/haematol.11220.

Stone, R. "CALGB 10603 (RATIFY): A randomized phase III study of induction (daunorubicin/cytarabine) and consolidation (high-dose cytarabine) chemotherapy combined with midostaurin or placebo in treatment-naive patients with FLT3 mutated AML" (2011) Paper presented at the ASCO. (Abstract Only).

Stone, et al. "Phase IB study of the FLT3 kinase inhibitor midostaurin with chemotherapy in younger newly diagnosed adult patients with acute myeloid leukemia" (2012) advance online publication, May 25, 2012, Leukemia, 26(9), 2061-2068. doi:10.1038/leu.2012.115.

Westhus, et al. "FLAG salvage therapy combined with idarubicin in relapsed/refractory acute myeloid leukemia" (2019). Leuk Lymphoma, 60(4), 1014-1022. doi:10.1080/10428194.2018.1508670.

Yavuz, et al. "IDA-FLAG regimen for the therapy of primary refractory and relapse acute leukemia: a single-center experience" (2006). Am J Ther, 13(5), 389-393. doi:10.1097/01.mjt.0000181690.21601.09.

Pratz, et al. "Incorporating FLT3 Inhibitors into acute myeloid leukemia treatment regimens" Leuk Lymphoma, May 2008, 49(5): 852-863. doi:10.1080/10428190801895352.

United States Patent & Trademark Office (ISA), International Search Report and Written Opinion for PCT/US2020/013066 dated May 19, 2020, 13 pp.

* cited by examiner

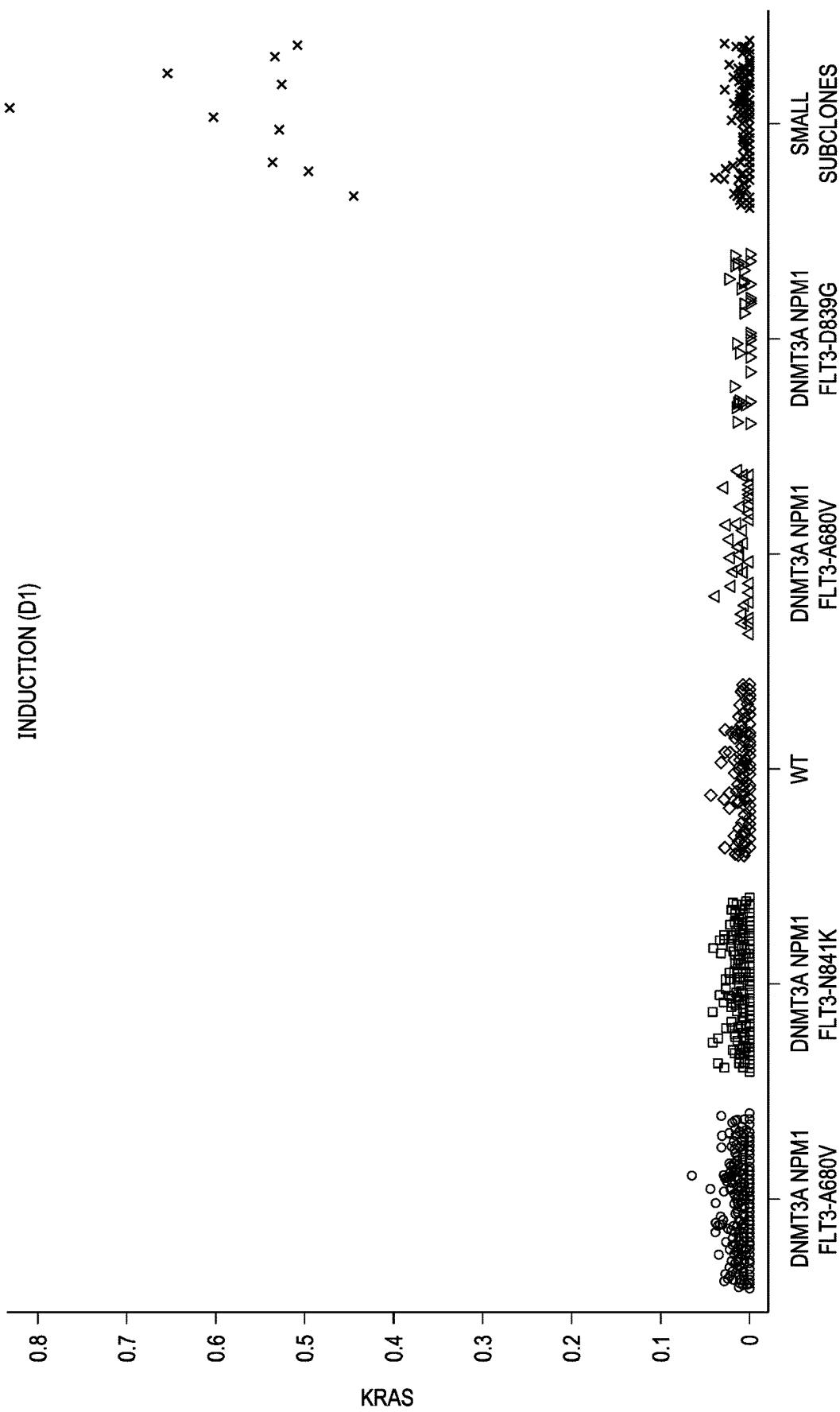

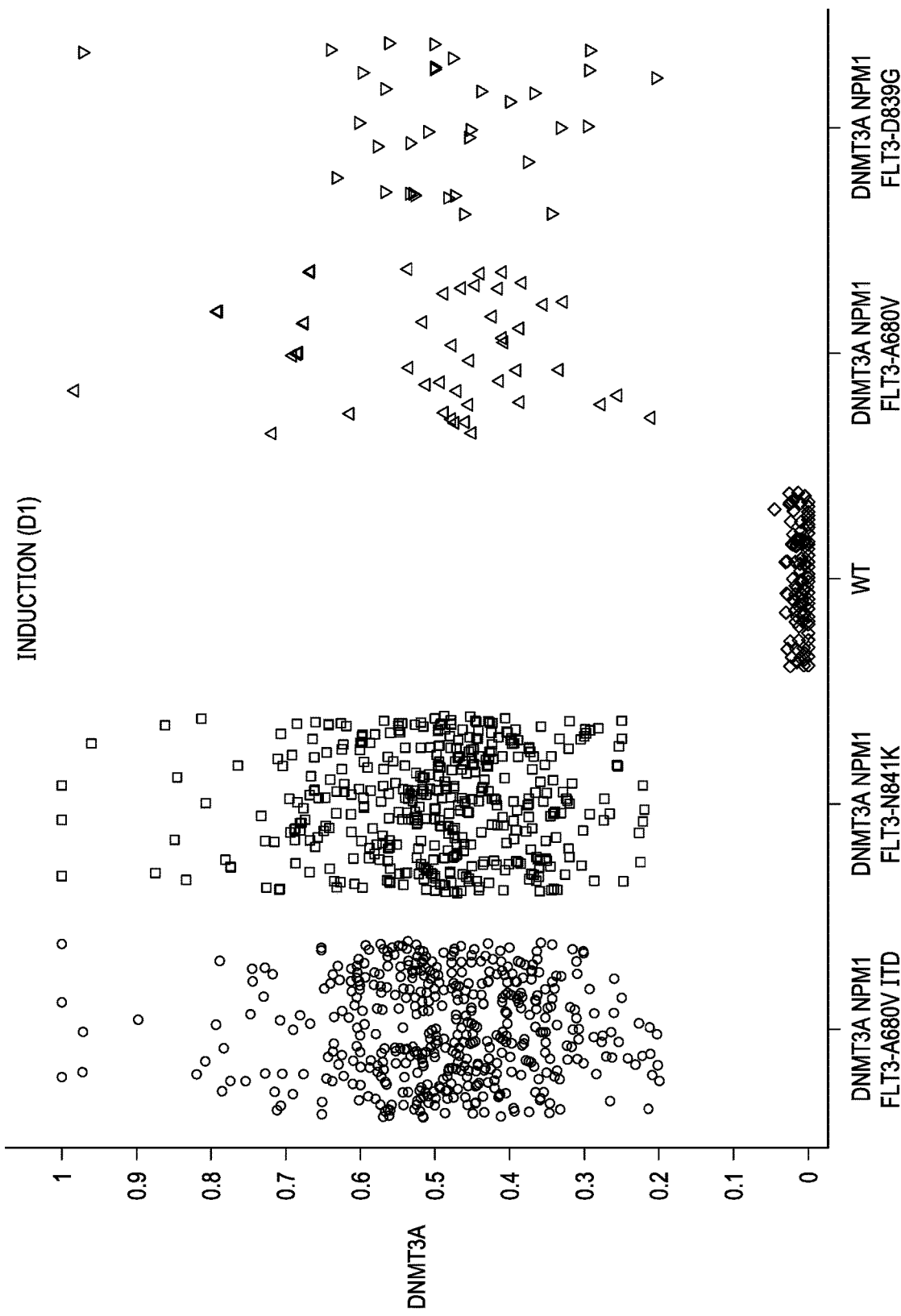

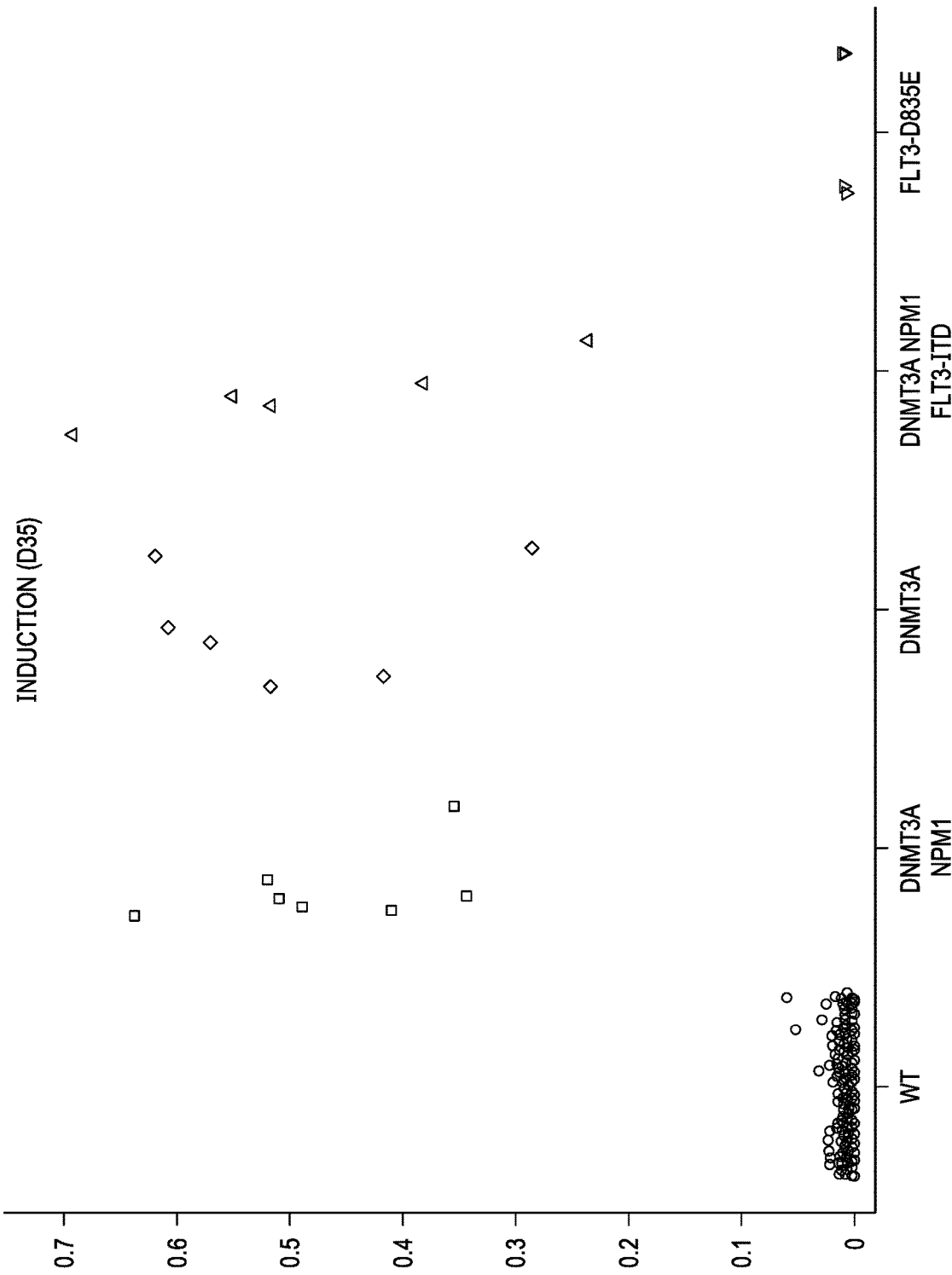

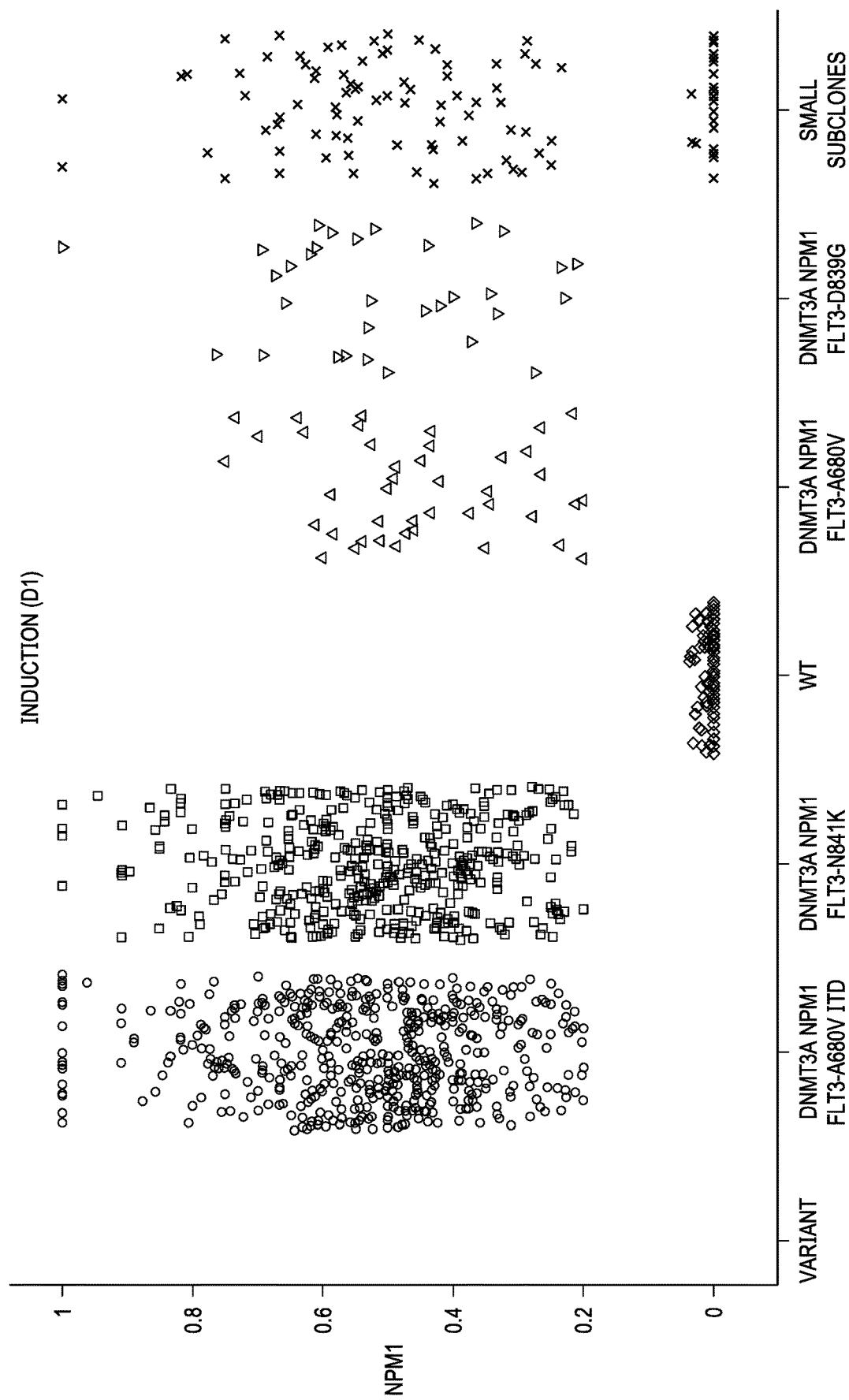

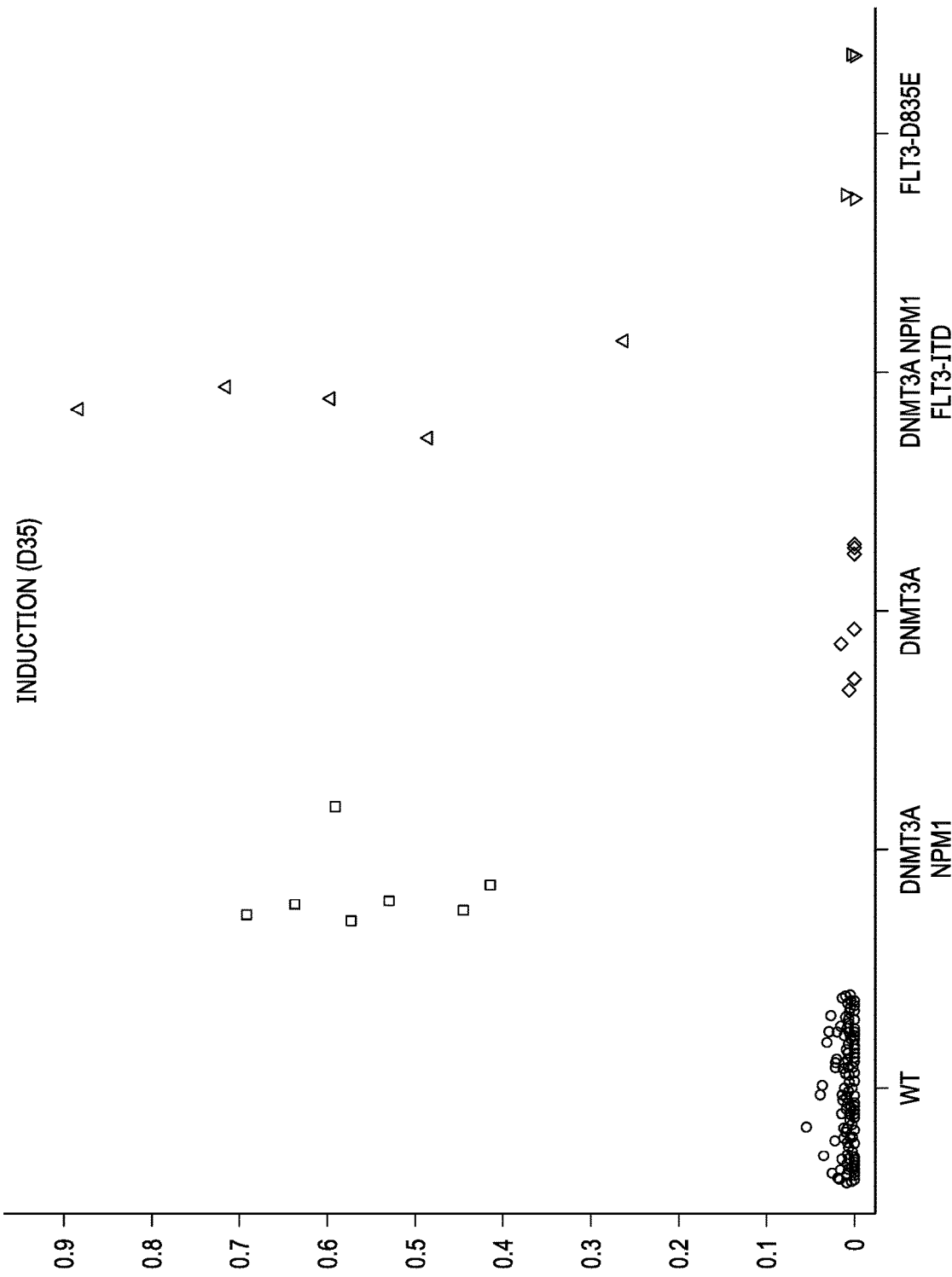

USES OF CRENOLANIB

CROSS-REFERENCE TO RELATED APPLICATIONS

This application claims priority to U.S. Provisional Application Ser. No. 62/888,717, filed Aug. 19, 2019, the entire contents of which are incorporated herein by reference.

TECHNICAL FIELD OF THE INVENTION

This invention pertains to methods of reducing or inhibiting the kinase activity of normal and mutated FLT3 in a cell or a subject by first detecting clonal heterogeneity and then using crenolanib to prevent or treat cell proliferative disorder(s) related to FLT3.

STATEMENT OF FEDERALLY FUNDED RESEARCH

Not applicable.

INCORPORATION-BY-REFERENCE OF MATERIALS FILED ON COMPACT DISC

Not applicable.

BACKGROUND OF THE INVENTION

Without limiting the scope of the invention, its background is described in connection with cancer treatments and the novel use of genetic assays to monitor measurable residual disease throughout the treatment course, determine the presence or absence of recurrent genetic mutations, and administer crenolanib, or a pharmaceutically acceptable salt thereof, to patients carrying the appropriate recurrent genetic mutations in order to remove the measurable residual disease and/or maintain disease remission.

Different proliferative diseases, such as leukemia, are often associated with a distinct pattern of recurrent genetic mutations or alterations. Acute myeloid leukemia (AML) in particular is associated with recurrent mutations in an array of genes such as FLT3, DNMT3A, NPM1, and others (Tyner et al., 2018). Due to the nature of leukemogenesis, AML is polyclonal and heterogeneous, with distinct subpopulations of cells expressing different combinations of genetic mutations. After treatment with chemotherapeutic or targeted agents, or a combination of these, a patient may achieve morphological complete remission but still retain a small percentage of cells with persistent leukemia-related mutations. This is known as measurable residual disease or MRD (Ding et al., 2012). Patients with MRD, though in morphological remission, may benefit from long-term treatment administration to prevent disease relapse. This type of treatment administration is often referred to as maintenance.

Mutations in the receptor tyrosine kinase FLT3 are associated with high risk of relapse and poor prognosis. It is also one of the more common genetic alterations in AML, occurring in approximately 20-30% of cases (Daver, Schlenk, Russell, & Levis, 2019). Mutations in FLT3 are also associated with other proliferative disorders. The frequency and prognostic value of mutations in this gene have made FLT3 a highly attractive drug target in proliferative disorders, especially hematologic malignances such as AML. Agents targeting this protein have recently been approved or are currently in development. One such agent currently in development is crenolanib, a tyrosine kinase inhibitor with significant activity against FLT3 mutations.

Due to the impact of FLT3 mutations on patient prognosis, persistence these mutations in MRD are of special concern. Traditional methods of monitoring measurable residual disease are limited by their inability to detect mutations in very small numbers of cells, or dependent on changes in the expression pattern of cell markers which may not be reliable over time or between institutions (Ommen, 2016). Therefore, what is needed is a method with improved sensitivity to detect recurrent genetic mutations that are associated with increased risk of relapse, allowing physicians to choose more appropriate methods or treatments and to remove or reduce measurable residual disease thereby maintaining disease remission.

SUMMARY OF THE INVENTION

The present invention includes a method of treating a subject with a proliferative disorder comprising a wild type FLT3 with or without one or more co-occurring FLT3 mutations, the method comprising of administering to the subject a therapeutically effective amount of crenolanib or a pharmaceutically acceptable salt thereof in combination with at least one of an alkylating agent, an antimetabolite, a natural product or a combination thereof. In another aspect a method of treating a subject with a proliferative disorder comprising a wild type FLT3 one or more co-occurring RAS mutations, the method comprising of administering to the subject a therapeutically effective amount of crenolanib or a pharmaceutically acceptable salt thereof in combination with at least one of an alkylating agent, an antimetabolite, a natural product or a combination thereof. In yet another aspect is a method of preventing a relapse of a proliferative disorder; comprising administering a therapeutically effective amount of crenolanib or a pharmaceutically acceptable salt thereof and as a single agent or in combination with another pharmaceutical agent. In one aspect where the proliferative disorder is characterized by comprising one or more function altering mutations and at least one recurrent genetic mutation. In one aspect, the minimal residual disease is detected by: obtaining a sample from the subject; single cell sequencing the genetic code of the abovementioned genes, wherein the sequencing comprises at least 1,000,000 reads/sample; and analyzing only samples were there is allele dropout rate of 10% or less. In another aspect, the presence or absence of one or more mutations is found in the abovementioned genes which create patient-specific single cell mutations profiles correlating with the proliferative disorder. In another aspect, the abovementioned recurrent genetic mutations are found in at least one of FLT3, NPM1, DNMT3A, NRAS, KRAS, JAK2, PTPN11, TET2, IDH1, IDH2, WT1, RUNX1, CEBPA, ASXL1, BCOR, SF3B1, U2AF1, STAG2, SETBP1, ZRSR2, GRB7, SRSF2, MLL, NUP98, ETV6, TCL1A, TUSC3, BRP1, CD36, TYK2, TP53, EZH2, GATA2, KIT, PHF6, MYC, ERG, MYD88, RAD21, STAT3, NF1, BRAF, KDM6A, SETBP1, CALR, CBL, KMT2A, PHF6, SMC1A, CHEK2, GNAS, PPMID, SMC3, ZRSR2, CSF3R, HRAS, MPL, PTEN, ATM, MUTYH, or others. In another aspect, the FLT3 mutations found include at least one of FLT3-ITD, FLT3-TKD, or other FLT3 mutation variants. In another aspect, the FLT3-TKD mutations include a point mutation resulting in an alteration or deletion in at least one F612, L616, K663, M664, M665, N676, A680, F691, A833, R834, D835, I836, D839, N841, Y842, or A848. In another aspect, the FLT3 variant mutations include a point mutations resulting in an alteration or deletion in at least one of L20, D324, K429, L442, E444, S451, V491, Y572, E573, L576, Y572, Y572, Q580, V591, T582, D586, Y589, V592, F594, E596, E598, Y599, D600, R607, A848 or others. In another aspect, the subject is a pediatric subject.

In another aspect, further comprising the steps of: repeating the steps (a) through (c) from one or more longitudinally successive samples from the subject, combining one or more longitudinal single cell genomic mutational profiles to determine the presence or absence of one or more mutations that changes as a response to administering a therapeutically effective amount of crenolanib or a pharmaceutically acceptable salt thereof and determining measurable residual disease status of said proliferative disorder from an increase or decrease of percentage of patient-specific singe cell mutational profiles after treatment that is correlated with said proliferative disorder. In another aspect, the sample obtained is at least one of bone marrow, peripheral blood, or tumor tissue. In another aspect, the single cell sequencing is comprised of using a single-cell multi-omic assay for detecting single nucleotide variants, copy number variants, and protein changes simultaneously from the same cell, such as a TAPESTRI™ platform, to prepare genomic DNA for the abovementioned genes with markers that are associated per cell, and sequencing said prepared DNA with at least one of MiSeq, HiSeq, or NovaSeq sequencing platforms. In another aspect, the subject is a pediatric subject.

In another embodiment, the present invention includes a method of treating a subject with a proliferative disorder that comprises a wild type FLT3 with one or more co-occurring RAS mutations, the method comprising administering to the subject a therapeutically effective amount of crenolanib or a pharmaceutically acceptable salt thereof in combination with at least one of alkylating agents, antimetabolite, natural product, or a combination thereof. In one aspect, a minimal residual disease of the proliferative disorder is detected by: (a) obtaining a sample from the subject comprising neoplastic cells; (b) single cell sequencing the sample wherein the sequencing comprises at least 1,000,000 reads/sample; and (c) analyzing the mutations from only samples with an allele dropout rate of 10% or less. In another aspect, a presence or absence of the one or more mutations is used to make a patient-specific single cell mutational profiles correlating with the proliferative disorder. In another aspect, the RAS mutation is at least one of an NRAS or a KRAS mutation. In another aspect, the one or more co-occurring mutations are at least one of FLT3, NPM1, DNMT3A, JAK2, PTPN11, TET2, IDH1, IDH2, WT1, RUNX1, CEBPA, ASXL1, BCOR, SF3B1, U2AF1, STAG2, SETBP1, ZRSR2, GRB7, SRSF2, MLL, NUP98, ETV6, TCL1A, TUSC3, BRP1, CD36, TYK2, TP53, EZH2, GATA2, KIT, PHF6, MYC, ERG, MYD88, RAD21, STAT3, NF1, BRAF, KDM6A, SETBP1, CALR, CBL, KMT2A, PHF6, SMC1A, CHEK2, GNAS, PPM1D, SMC3, ZRSR2, CSF3R, HRAS, MPL, PTEN, ATM, or MUTYH. In another aspect, method further comprising the steps of: repeating the steps (a) through (c) from one or more longitudinally successive samples from the subject; combining one or more longitudinal single cell genomic mutational profiles to determine a presence or absence of the one or more mutations that change in response to administering a therapeutically effective amount of crenolanib or a pharmaceutically acceptable salt thereof; and determining a measurable residual disease status of the proliferative disorder measured as an increase or decrease of percentage of patient-specific single cell mutational profiles after treatment that are correlated with the proliferative disorder. In another aspect, the sample obtained is at least one of bone marrow, peripheral blood or tumor tissue. In another aspect, the single cell sequencing comprises preparing genomic DNA with one or more markers per cell, and sequencing the prepared DNA. In another aspect, the single cell sequencing uses aMiSeq, HiSeq, or NovaSeq platform. In another aspect, the alkylating agent is selected from at least one of: carmustine, chlorambucil, cyclophosphamide, ifosfamide, lomustine, streptozotocin, temozolomide, cisplatin, carboplatin, nedaplatin, or oxaliplatin. In another aspect, the antimetabolite is selected from at least one of: methotrexate, pemetrexed, ralititrexed, cytarabine, fludarabine, fluorouracil, floxuridine, capcitabine, or gemcitabine. In another aspect, the natural product is selected from at least one of: vinblastine, vinorelbine, vincristine, vindesine, vinflunine, paclitaxel, docetaxel, cabazitaxel, etoposide, teniposide, topotecan, irinotecan, daunorubicin, doxorubicin, idarubicin, eiprubicin, valrubicin, mitoxantrone, bleomycin, estramustine, and/or mitomycin. In another aspect, the subject further comprises a mutant FLT3 tyrosine kinase. In another aspect, the subject is a pediatric patient.

In another embodiment, the present invention includes a method of preventing a relapse of a proliferative disorder in a subject previously treated to be free of the proliferative disorder comprising administering to the subject a therapeutically effective amount of crenolanib or a pharmaceutically acceptable salt thereof for a sufficient period of time following a response to induction chemotherapy, consolidation, or following hematopoietic stem cell transplantation to prevent the relapse of the proliferative disorder. In one aspect, the proliferative disorder is characterized by comprising one or more function altering mutations and at least one recurrent genetic mutation. In another aspect, the proliferative disorder is characterized by comprising a wild type FLT3 with or without one or more co-occurring mutations. In another aspect, the subject was previously treated with: an alkylating agent is selected from at least one of: carmustine, chlorambucil, cyclophosphamide, ifosfamide, lomustine, streptozotocin, temozolomide, cisplatin, carboplatin, nedaplatin, or oxaliplatin; an antimetabolite is selected from at least one of: methotrexate, pemetrexed, ralititrexed, cytarabine, fludarabine, fluorouracil, floxuridine, capcitabine, or gemcitabine; or a natural product is selected from at least one of: vinblastine, vinorelbine, vincristine, vindesine, vinflunine, paclitaxel, docetaxel, cabazitaxel, etoposide, teniposide, topotecan, irinotecan, daunorubicin, doxorubicin, idarubicin, eiprubicin, valrubicin, mitoxantrone, bleomycin, estramustine, and/or mitomycin. In another aspect, the one or more co-occurring mutations are at least one of: NPM1, DNMT3A, NRAS, KRAS, JAK2, PTPN11, TET2, IDH1, IDH2, WT1, RUNX1, CEBPA, ASXL1, BCOR, SF3B1, U2AF1, STAG2, SETBP1, ZRSR2, GRB7, SRSF2, MLL, NUP98, ETV6, TCL1A, TUSC3, BRP1, CD36, TYK2, TP53, EZH2, GATA2, KIT, PHF6, MYC, ERG, MYD88, RAD21, STAT3, NF1, BRAF, KDM6A, SETBP1, CALR, CBL, KMT2A, PHF6, SMC1A, CHEK2, GNAS, PPMID, SMC3, ZRSR2, CSF3R, HRAS, MPL, PTEN, ATM, or MUTYH. In another aspect, the subject is a pediatric patient.

The present invention provides methods of reducing measurable residual disease in a subject with a proliferative disorder. Other features and advantages of the invention will be apparent from the following detailed description of the invention and from the claims.

BRIEF DESCRIPTION OF THE DRAWINGS

For a more complete understanding of the features and advantages of the present invention, reference is now made to the detailed description of the invention along with the accompanying figures and in which:

FIGS. 2A and 2B are scatter plots showing individual cells expressing mutant KRAS (y-axis) within bone marrow samples of a patient at diagnosis (FIG. 2A) and 35 days following the start of induction (FIG. 2B). FIG. 2A shows that the cell populations contain the following mutations from left to right; DNMT3A/NPM1/FLT3-A680V/FLT3-ITD, DNMT3A/NPM1/FLT3-N841K, wild type, DNMT3A/NPM1/FLT3-A680V, DNMT3A/NPM1/FLT3-D839G and lastly small subclonal cells with various mutations. FIG. 2B shows that the cell populations are as follows: wild type, DNMT3A/NPM1, DNMT3A, and DNMT3A/NPM1/FLT3-ITD. Treatment with crenolanib eliminated the vast majority of the mutant containing cancer cell populations.

FIGS. 3A and 3B are scatter plots showing individual cells expressing mutant DNMT3 (y-axis) within bone marrow samples of a patient at diagnosis (FIG. 3A) and 35 days following the start of induction (FIG. 3B). FIG. 3A shows that the cell populations contain the following mutations from left to right; DNMT3A/NPM1/FLT3-A680V/FLT3-ITD, DNMT3A/NPM1/FLT3-N841K, wild type, DNMT3A/NPM1/FLT3-A680V, and DNMT3A/NPM1/FLT3-D839G. FIG. 3B shows that the cell populations are as follows: wild type, DNMT3A/NPM1, DNMT3A, DNMT3A/NPM1/FLT3-ITD, and FLT3-D835E. Treatment with crenolanib eliminated the vast majority of the mutant containing cancer cell populations.

FIGS. 4A and 4B are scatter plots showing individual cells expressing mutant NPM1 (y-axis) within bone marrow samples of a patient at diagnosis (FIG. 4A) and 35 days following the start of induction (FIG. 4B). FIG. 4A shows that the cell populations contain the following mutations from left to right; DNMT3A/NPM1/FLT3-A680V/FLT3-ITD, DNMT3A/NPM1/FLT3-N841K, wild type, DNMT3A/NPM1/FLT3-A680V, and DNMT3A/NPM1/FLT3-D839G, and lastly small subclonal cells with various mutations. FIG. 4B shows that the cell populations are as follows: wild type, DNMT3A/NPM1, DNMT3A, DNMT3A/NPM1/FLT3-ITD, and FLT3-D835E. Treatment with crenolanib eliminated the vast majority of the mutant containing cancer cell populations.

DETAILED DESCRIPTION OF THE INVENTION

Figure 1:
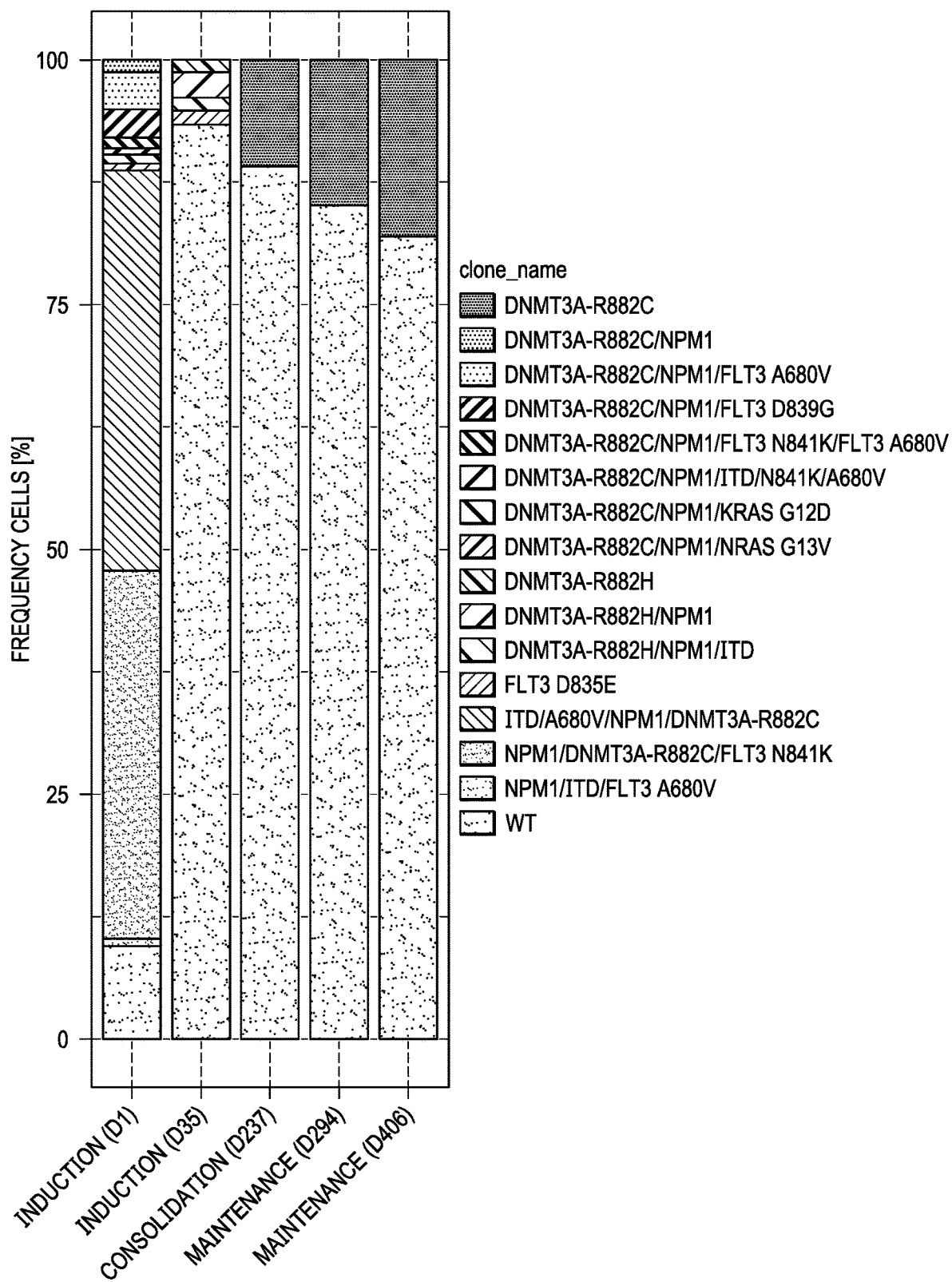
FIG. 1 is an illustration of longitudinal bone marrow samples of a patient. Normal wild-type (WT) cells are displayed in grey. The illustration represents total sub-clonal populations within samples at diagnosis, 35 days following the start of induction, and three timepoints during maintenance. Samples indicate that variant FLT3 and FLT3 activating mutations were eliminated with combination therapy of intensive induction chemotherapy in addition with crenolanib, high-dose cytarabine (HiDAC) consolidation with crenolanib, and single agent crenolanib maintenance for mutational clearance.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but include the general class of which a specific example may be used for illustration. The terminology herein is used to describe specific embodiments of the invention, but their usage does not delimit the invention, except as outlined in the claims.

Definitions

As used herein, the terms "measurable residual disease", "minimal residual disease", and "MRD" refer to a situation or condition where, by traditional methods (including but not limited to cytogenetics, histology), there is no evidence of cancer detectable in a subject. While there may be remaining tumor cells in the body, these are found at quantities beneath the limit of detection of traditional methods. These residual tumor cells, however, are fully capable of recapitulating the proliferative disease. MRD typically occurs after a complete response or complete remission following chemotherapy, radiation therapy, and/or allogenic stem cell transplant. MRD detection methods known in the art include flow cytometry-based methods that monitor the presence of prespecified cell expression markers and molecular based approaches. Molecular based approaches to MRD detection include PCR-based testing for the presence of mutations, e.g., NPM1, DNMT3A, NRAS, KRAS, JAK2, PTPN11, TET2, IDH1, IDH2, WT1, RUNX1, CEBPA, ASXL1, BCOR, SF3B1, U2AF1, STAG2, SETBP1, ZRSR2, GRB7, SRSF2, MLL, NUP98, ETV6, TCL1A, TUSC3, BRP1, CD36, TYK2, TP53, EZH2, GATA2, KIT, PHF6, MYC, ERG, MYD88, RAD21, STAT3, NF1, BRAF, KDM6A, SETBP1, CALR, CBL, KMT2A, PHF6, SMC1A, CHEK2, GNAS, PPM1D, SMC3, ZRSR2, CSF3R, HRAS, MPL, PTEN, ATM, or MUTYH. PCR-based approaches can be used for patients harboring one or more of these genetic abnormalities.

As used herein, the term "subject" refers to an animal, such as a mammal or a human, who has been the object of treatment, observation or experiment. In certain examples, the mammal or human is pediatric.

As used herein, the terms "proliferative disorder(s)" and "cell proliferative disorder(s)" refer to excess cell proliferation of one or more subset of cells in a multicellular organism resulting in harm (i.e. discomfort or decreased life expectancy) to the multicellular organism. Cell proliferative disorders can occur in different types of animals and humans. As used herein, "cell proliferative disorders" include neoplastic disorders.

As used herein, the term "neoplastic disorder" refers to a tumor resulting from abnormal or uncontrolled cellular growth. Examples of neoplastic disorders include, but are not limited to the following disorders, for instance: cancers such as carcinoma, lymphoma, blastoma, sarcoma, and leukemias. Non-limiting examples of proliferative disorders for treatment with the present invention include bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell cancer lung cancer, squamous cell cancer, skin cancer, stomach cancer, testicular cancer, thyroid cancer, uterine cancer, glioma cancer, and gastric cancer. As used herein, the term "neoplastic disorder" refers to a tumor resulting from abnormal or uncontrolled cellular growth. Examples of neoplastic disorders include, but are not limited to the following disorders, for instance: cancers such as carcinoma, lymphoma, blastoma, sarcoma, and leukemias. Non-limiting examples of proliferative disorders for treatment with the present invention include bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell cancer lung cancer, squamous cell cancer, skin cancer, stomach cancer, testicular cancer, thyroid cancer, uterine cancer, glioma cancer, and gastric cancer.

As used herein the term "recurrent genetic mutations" refers to one or more genetic mutations that are frequently found in proliferative disorders, many of which are known to be highly heterogenous diseases. Many recurrent mutations have been shown to impact disease outcome. Examples of recurrent genetic mutations include, but are not limited to mutations in NPM1, DNMT3A, NRAS, KRAS, JAK2, PTPN11, TET2, IDH1, IDH2, WT1, RUNX1, CEBPA, ASXL1, BCOR, SF3B1, U2AF1, STAG2, SETBP1, ZRSR2, GRB7, SRSF2, MLL, NUP98, ETV6, TCL1A, TUSC3, BRP1, CD36, TYK2, TP53, EZH2, GATA2, KIT, PHF6, MYC, ERG, MYD88, RAD21, STAT3, NF1, BRAF, KDM6A, SETBP1, CALR, CBL, KMT2A, PHF6, SMC1A, CHEK2, GNAS, PPM1D, SMC3, ZRSR2, CSF3R, HRAS, MPL, PTEN, ATM, or MUTYH, specifically, mutations of these genes that lead to a proliferative disease and/or cancer.

As used herein the term "function altering mutation" refers to one or more genetic mutations that result in a mutated protein, which has different activity compared with the wild-type protein. This includes mutations that result in loss of function, where the mutant no longer has the function of wild-type, and gain of function, wherein the mutant has an additional function that the wild-type did not have. Also included in this are activating mutations, wherein the mutant has the same activity of the wild-type; however, the mutant is lacking the negative regulation that controls wild-type signaling.

As used herein, the term "therapeutically effective amount" refers to an amount of crenolanib or a pharmaceutically acceptable salt thereof, administered to a subject as a single agent or in combination with another pharmaceutical agent(s), e.g., a chemotherapeutic agent, that in combination elicits the biological or medicinal response in a subject that is being sought by a researcher, veterinarian, medical doctor, or other clinician, which includes alleviation of the symptoms of the disease or disorder being treated. Methods for determining therapeutically effective doses for pharmaceutical compositions comprising a compound of the present invention are known in the art. Techniques and compositions for making useful dosage forms using the present invention are described in many references, including: P. O. Anderson, J. E. Knoben, and W. G. Troutman, Handbook of clinical drug data, 10th ed. New York; Toronto: McGraw-Hill Medical Pub. Division, 2002, pp. xvii, 1148 p (Anderson, Knoben, & Troutman, 2002); A. Goldstein, W. B. Pratt, and P. Taylor, Principles of drug action: the basis of pharmacology, 3rd ed. New York: Churchill Livingstone, 1990, pp. xiii, 836 p. (Goldstein, Pratt, & Taylor, 1990); B. G. Katzung, Basic & clinical pharmacology, 9th ed. (Lange medical book). New York: Lange Medical Books/McGraw Hill, 2004, pp. xiv, 1202 p. (Katzung, 2004); L. S. Goodman, J. G. Hardman, L. E. Limbird, and A. G. Gilman, Goodman and Gilman's the pharmacological basis of therapeutics, 10th ed. New York: McGraw-Hill, 2001, pp. xxvii, 2148 p. (Goodman, Hardman, Limbird, & Gilman, 2001); J. P. Remington and A. R. Gennaro, Remington: the science and practice of pharmacy, 20th ed. Baltimore, Md.: Lippincott Williams & Wilkins, 2000, pp. xv, 2077 p; W. Martindale, J. E. F. Reynolds, and Royal Pharmaceutical Society of Great Britain. Council, The extra pharmacopoeia, 31st ed. London: Royal Pharmaceutical Society, 1996, pp. xxi, 2739; and G. M. Wilkes, Oncology Nursing Drug Handbook 2016, 20 ed. Sudbury: Jones & Bartlett Publishers, 2016, p. 1500 p. (Wilkes, 2016), relevant portions of each are incorporated herein by reference.

As used herein, the phrase "in combination with" refers to the administration of crenolanib or a pharmaceutically acceptable salt thereof, and another pharmaceutical agent(s) either simultaneously or sequentially in any order, such as, for example, at repeated intervals as during a standard course of treatment for a single cycle or more than one cycle, such that one agent can be administered prior to, at the same time, or subsequent to the administration of the other agents, or any combination thereof.

As used herein, the term "chemotherapeutic agent" refers to anti-cell proliferation therapies such as alkylating agents, antimetabolites, and natural products. Chemotherapy is known to those skilled in the art and the appropriate dosage(s) and scheme(s) for chemotherapy will be similar to those already employed in clinical therapies wherein the chemotherapy is delivered in combination with other therapies or used alone. A variety of chemotherapeutic agents may be used in combination with the present invention. By way of example only, taxane compounds (such as docetaxel), are safely administered in combination in the compound of the present invention in a dosage of 75 mg per square meter (mg/m$^2$) of body surface area. The skilled artisan will recognize that the selected chemotherapeutic will have a dosage based on a variety of factors, such as the weight, age, gender, extent of disease, etc., that will change the dosage within best medical practice for the intended treatment.

As used herein, the term "alkylating agent" refers to a group of chemotherapies that classically have caused the addition of an alkyl group to DNA but is now used to refer to any chemotherapy that causes addition of a small chemical moiety to DNA. Examples of alkylating agents include, but are not limited to carmustine, chlorambucil, cyclophosphamide, ifosfamide, lomustine, streptozotocin, temozolomide, cisplatin, carboplatin, nedaplatin, and/or oxaliplatin.

As used herein, the term "antimetabolite" refers to a group of chemotherapies that structurally similar to a naturally occurring chemical in the body that it can take the place of said chemical in binding to an enzyme or protein but are different enough that they prohibit the termination of the normal action of the chemical in the body. Examples of antimetabolites include, but are not limited to methotrexate, pemetrexed, ralititrexed, cytarabine, fludarabine, fluorouracil, floxuridine, capcitabine, and/or gemcitabine.

As used herein, the term "natural products" refers to a group of chemotherapeutic agents and/or chemotherapies that are purified organic compounds originally isolated from a living organism that are produced by pathways of secondary metabolism. Examples of 20 natural products includes but is not limited to vinblastine, vinorelbine, vincristine, vindesine, vinflunine, paclitaxel, docetaxel, cabazitaxel, etoposide, teniposide, topotecan, irinotecan, daunorubicin, doxorubicin, idarubicin, eiprubicin, valrubicin, mitoxantrone, bleomycin, estramustine, and/or mitomycin.

As used herein, the term "composition" refers to a product comprising the specified ingredients in the specified amounts, as well as any product that results, directly or indirectly, from combinations of the specified ingredients in the specified amounts.

Single cell DNA sequencing allows for the analysis of recurrent genetic mutations at the single cells level. This removes earlier barriers in monitoring measurable residual disease due to the relatively high limit of detection and other disadvantages of tradition methods (Eastburn et al., 2017). To date, such methods have primarily been used in the academic lab setting to characterize the genetic mutations associated with a particular disease, to discover novel potential recurrent mutations, or to characterize genetic mutations or alterations that may confer resistance to treatment agents. However, these methods have a potential powerful use: to monitor measurable residual disease in patients in order to determine if a patient may benefit from the administration of a particular treatment or intervention in order to achieve or maintain disease remission.

The present invention is based, at least in part, on the discovery that following treatment of standard chemo given sequentially with crenolanib, or crenolanib monotherapy that MRD was reduced or eliminated over the course of treatment in subjects, as well as isolated cells in the blood or bone marrow of subjects with a proliferative disorder. The present intention comprises the use of compounds of the present invention with standard chemotherapy to reduce or eliminate MRD in a subject with at least one recurrent genetic mutation(s) as measured by single cell genomic sequencing.

Crenolanib (4-Piperidinamine, 1-[2-[5-[(3-methyl-3-oxetanyl) methoxy]-1H-benzimidazol-1-yl]-8-quinolinyl]) and its pharmaceutically acceptable salts, including but not limited to: Crenolanib Besylate, Crenolanib Phosphate, Crenolanib Lactate, Crenolanib Hydrochloride, Crenolanib Citrate, Crenolanib Acetate, Crenolanib Toluenesulphonate and Crenolanib Succinate, but may also be made available free of salts. Preparation of the compounds of the present invention. General synthetic methods for preparing the compounds of Formula I are provided in, e.g., U.S. Pat. No. 5,990,146 (issued Nov. 23, 1999) (Warner-Lambert Co.) and PCT published application numbers WO 99/16755 (published Apr. 8, 1999) (Merck & Co.) WO 01/40217 (published Jul. 7, 2001) (Pfizer, Inc.), US Patent Application Publication No. US 2005/0124599 (Pfizer, Inc.) and U.S. Pat. No. 7,183,414 (Pfizer, Inc.), relevant portions incorporated herein by reference. Crenolanib is a protein tyrosine kinase inhibitor selective for constitutively active FLT3 mutations, including FLT3 ITD and FLT3 TKD mutations. Unlike prior FLT3 inhibitors in the art, the besylate salt form of crenolanib has been shown to be remarkably effective in depleting circulating peripheral blood blast percentages and bone marrow blast percentages in heavily pretreated FLT3 mutant AML. Crenolanib is currently being investigated for use in the treatment of patients with newly diagnosed FLT3 mutated AML and relapsed or refractory constitutively activated FLT3 mutated primary AML or AML secondary to myelodysplastic in combination with standard chemotherapy.

In one embodiment, the present invention therapeutically effective amounts of the compound having formula I:

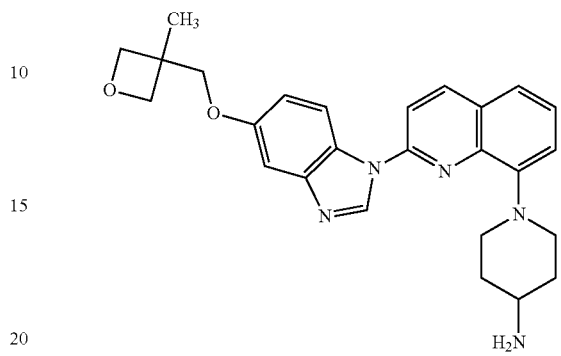

or a pharmaceutically acceptable salt or solvate thereof, in a therapeutically or prophylactically effective amount against a proliferative disease is selected from at least one of a leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy. Pharmaceutically acceptable salts including hydrochloride, phosphate and lactate are prepared in a manner similar to the benzenesulfonate salt and are well known to those of moderate skill in the art.

Compounds of the present invention may be administered to a subject systemically, for example, orally, intravenously, subcutaneously, intramuscular, intradermal or parenterally. The compounds of the present invention can also be administered to a subject locally.

Compounds of the present invention may be formulated for slow-release or fast-release with the objective of maintaining contact of compounds of the present invention with targeted tissues for a desired range of time.

Compositions suitable for oral administration include solid forms, such as pills, tablets, caplets, capsules, granules, and powders, liquid forms, such as solutions, emulsions, and suspensions. Forms useful for parenteral administration include sterile solutions, emulsions and suspensions.

The daily dosage of the compounds of the present invention may be varied over a wide range from 15 to 500, 25 to 450, 50 to 400, 100 to 350, 150 to 300, 200 to 250, 15, 25, 50, 75, 100, 150, 200, 250, 300, 400, 450, or 500 mg per day. The compounds of the present invention may be administered on a daily regimen, once, twice, three or more times per day. Optimal doses to be administered may be determined by those skilled in the art and will vary with the compound of the present invention used, the mode of administration, the time of administration, the strength of the preparation, the details of the disease condition. One or more factors associated with subject characteristics, such as age, weight, and diet will call for dosage adjustments. Techniques and compositions for making useful dosage forms using the Crenolanib are described in one or more of the following references: Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins, 2000; Martindale, The Extra Pharmacopoeia, Thirty-Second Edition (The Pharmaceutical Press, London, 1999); relevant portions incorporated herein by reference.

A dosage unit for use of Crenolanib, may be a single compound or mixtures thereof with other compounds, e.g., a potentiator. The compounds may be mixed together, form ionic or even covalent bonds. The compounds of the present invention may be administered in oral, intravenous (bolus or infusion), intraperitoneal, subcutaneous, or intramuscular form, all using dosage forms well known to those of ordinary skill in the pharmaceutical arts. Depending on the particular location or method of delivery, different dosage forms, e.g., tablets, capsules, pills, powders, granules, elixirs, tinctures, suspensions, syrups, and emulsions may be used to provide the compounds of the present invention to a patient in need of therapy that includes the compound of Formula I.

The Crenolanib is typically administered in admixture with suitable pharmaceutical salts, buffers, diluents, extenders, excipients and/or carriers (collectively referred to herein as a pharmaceutically acceptable carrier or carrier materials) selected based on the intended form of administration and as consistent with conventional pharmaceutical practices. Depending on the best location for administration, the Crenolanib may be formulated to provide, e.g., maximum and/or consistent dosing for the particular form for oral, rectal, topical, intravenous injection or parenteral administration. While the Crenolanib may be administered alone, it will generally be provided in a stable salt form mixed with a pharmaceutically acceptable carrier. The carrier may be solid or liquid, depending on the type and/or location of administration selected.

Preparation of the compounds of the present invention. General synthetic methods which may be referred to for preparing the compounds of formula I are provided in U.S. Pat. No. 5,990,146 (issued Nov. 23, 1999) (Warner-Lambert Co.) and PCT published application numbers WO 99/16755 (published Apr. 8, 1999) (Merck & Co.) WO 01/40217 (published Jul. 7, 2001) (Pfizer, Inc.), US Patent Application Publication No. US 2005/0124599 (Pfizer, Inc.) and U.S. Pat. No. 7,183,414 (Pfizer, Inc.), relevant portions incorporated herein by reference.

Pharmaceutically acceptable salts such as hydrochloride, phosphate and lactate are prepared in a manner similar to the benzenesulfonate salt and are well known to those of moderate skill in the art. The following representative compounds of the present invention are for exemplary purposes only and are in no way meant to limit the invention, including Crenolanib as Crenolanib Besylate, Crenolanib Phosphate, Crenolanib Lactate, Crenolanib Hydrochloride, Crenolanib Citrate, Crenolanib Acetate, Crenolanib Toluenesulphonate and Crenolanib Succinate.

The present invention also provides both prophylactic and therapeutic methods for treating a subject at risk or susceptible to developing a cell proliferative disorder driven by aberrant kinase activity of the FLT3 receptor tyrosine kinase. In one example, the invention provides methods for preventing a cell proliferative disorder related to FLT3, comprising administration of a prophylactically effective amount of a pharmaceutical composition comprising a compound of the present invention in a subject. Administration of said prophylactic agent can occur prior to the manifestation of symptoms characteristic of the FLT3 driven cell proliferative disorder, such that a disease or disorder is prevented or, alternatively, delayed in its progression.

As used herein, the terms "mutant FLT3", "disorder related to FLT3," or "disorders related to FLT3 receptor," or "disorders related to FLT3 receptor tyrosine kinase," or "FLT3 driven cell proliferative disorder" refers to diseases associated with or implicating FLT3 activity, for example, mutations leading to constitutive activation of FLT3. Examples of "disorders related to FLT3" include disorders resulting from over stimulation of FLT3 due to mutations in FLT3, or disorders resulting from abnormally high amount of FLT3 activity due to abnormally high amount of mutations in FLT3. It is known that over-activity of FLT3 has been implicated in the pathogenesis of many diseases, including the following listed cell proliferative disorders, neoplastic disorders and cancers.

In mutated FLT3 tumors, the alteration in expression or presence of one or more genetic mutations or deletions within coding or intron-exon boundary regions, can lead to a decrease in prognosis. In addition to a pre-existing FLT3 mutation, the additional genetic mutations disclosed herein significantly decrease the prognosis of the patient. A poor prognosis can refer to any negative clinical outcome, such as, but not limited to, a decrease in likelihood of survival (such as overall survival, relapse-free survival, or metastasis-free survival), a decrease in the time of survival (e.g., less than 5 years, or less than one year), presence of a malignant tumor, an increase in the severity of disease, a decrease in response to therapy, an increase in tumor recurrence, an increase in metastasis, or the like. In particular examples, a poor prognosis is a decreased chance of survival (for example, a survival time of equal to or less than 60 months, such as 50 months, 40 months, 30 months, 20 months, 12 months, 6 months or 3 months from time of diagnosis or first treatment).

In one aspect of the invention pertains to single cell sequencing analysis of recurrent AML genetic mutations that is performed using the TAPESTRI™ platform. To use said platform, a cell suspension is introduced onto the platform using microfluidics, and each cell is then encapsulated in an oil droplet along with a protease to aid in DNA isolation. Cells are then lysed and loaded back onto the TAPESTRI™ platform, where each single nucleus is encapsulated with a unique DNA based barcode linked to acrylamide-based beads and PCR master mix and primer sets against recurrent AML mutant genes in an oil droplet. These droplets are directly deposited in PCR tubes and exposed to UV light to release the barcodes. Subsequently the barcoded genomic DNA within the droplets can be amplified according to standard PCR amplification techniques. In this same aspect the PCR products are then isolated using standard molecular biology techniques and then libraries prepared for next-generation sequencing compatible with Illumina platforms (including MiSeq, HiSeq, and NovaSeq), followed by sequencing said libraries on one of the validated Illumina platforms (including MiSeq, HiSeq, and NovaSeq). In the same aspect, the sequencing contains at least 1,000,000 reads per sample, and the allele dropout out rate is at most 10%. Next-generation sequencing data can be analyzed at least one of but not limited to using TAPESTRI Pipeline to generate genetic variant calls followed by TAPESTRI Insight for final analysis including determining co-occurring genetic mutations, or standard next generation sequencing (NGS) analysis methods known to one skilled in the art.

In one embodiment, the presence or absence of one or more mutations within the recurrent AML mutated genes creating a patient-specific single cell mutational profile correlating with the proliferative disorder.

In one aspect, repeating the abovementioned steps on at least one additional longitudinally successive samples from said subject, and then combine the longitudinal single cell genomic mutations profiles to determine the presence or absence of one or more mutations that change in response to chemotherapy in combination with a FLT3 TKI over time, thereby giving a method to determine MRD status from an increase or decrease of percentage of patient specific single cell mutational profiles following treatment.

In another embodiment the samples to be tested in the methods of the present invention comprises bone marrow or peripheral blood.

In one embodiment, the method of the present invention comprises using the TAPESTRI™ platform to prepare genomic DNA for the recurrent AML genetic mutations for individual cells, with said genomic DNA then being sequenced on an Illumina sequencing platform, including but not limited to MiSeq, HiSeq, and NovaSeq.

The present invention also includes methods for the removal of measurable residual disease in a subject suffering from a proliferative disorder, comprising administering to said patient a therapeutically effective amount of crenolanib or a pharmaceutically acceptable salt thereof and standard chemotherapy against a proliferative disease characterized by deregulated FLT3 activity and at least one recurrent AML genetic mutation is selected from one of leukemia, myeloma, myeloproliferative disease, myelodysplastic syndrome, Hodgkin's disease, myeloma, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL AML, with trilineage myelodysplasia (AMLITMDS), mixed lineage leukemia (MLL), myelodysplastic syndromes (MDSs), myeloproliferative disorders (MPD), or multiple myeloma (MM).

The present invention includes the follow method of preparing single cell DNA sequencing. One example is a single-cell multi-omic assay for detecting single nucleotide variants, copy number variants, and protein changes simultaneously from the same cell, such as TAPESTRI™. Mononuclear cells were isolated from bone marrow samples via FICOLL-PAQUE® gradient, resuspended in a 10% DMSO solution and frozen at −20° C. until needed. Single cell suspensions were prepared from thawed mononuclear cell samples to final concentrations indicated by the manufacturer's instructions, then loaded onto the TAPESTRI™ instrument. According to the manufacturer, the TAPESTRI™ platform uses microfluidics to separate single cells, encapsulate each cell within a lipid droplet, proteases are added to each droplet to aid in DNA isolation. Cell encapsulation, targeted PCR, and next generation library preparation were performed per the TAPESTRI™ platform's manufacturer's instructions using the TAPESTRI™ platform and the Thermo Fisher SimpliAmp thermal cycler (cat #A24811, or equivalent). The prepared single-cell DNA library was sequenced using Illumina's MiSeq instrument, per the manufacturer's instructions. Analysis of these next-generation sequencing data was performed by first processing the sequencing data using the TAPESTRI Pipeline (available on the Mission Bio website) to ultimately generate variant calls. The resultant loom files are then imported into the TAPESTRI™ bioinformatics software, Insight, which is used to identify relevant variants, including co-occurring and rare mutations.

Example 1

A 54-year-old female was diagnosed with AML with monocytic differentiation in 2016. This patient presented with 63% bone marrow blasts. At diagnosis, molecular testing using bulk DNA sequencing methods revealed the patient had FLT3-ITD, FLT3-N814K, FLT3-A680V, DNMT3A, and NPM1 mutations. This is a case of a particularly high-risk patient, having multiple FLT3 mutations associated with poor prognosis, having co-occurrence of NPM1-FLT3$^{ITD}$-DNMT3A mutations is also associated with a poor prognosis (Papaemmanuil et al., 2016). Furthermore, monocytic differentiation has been associated with CD163 overexpression, which has been retrospectively seen in the diagnostic bone marrow sample from this patient, and is also associated with poor prognosis (van Galen et al., 2019). To treat this patient's disease and overcome the FLT3 mutations, this patient was provided oral crenolanib besylate in combination with standard chemotherapy on a clinical trial for newly diagnosed AML patients with activating FLT3 mutations. The patient was treated with induction chemotherapy, comprised of seven days of cytarabine and three days of daunorubicin, followed by 100 mg of crenolanib besylate three times daily starting on day 10 of treatment.

A bone marrow biopsy taken on day 35 of treatment revealed the patient's bone marrow blasts had been reduced to less than 5% and the patient was determined to have achieved morphologic complete remission in response to crenolanib with combination therapy. In an effort to maintain remission, the patient was then administered four cycles of high dose cytarabine consolidation chemotherapy. In each cycle, the patient received cytarabine chemotherapy at standard doses, followed by oral crenolanib besylate at 100 mg three times daily starting 48 hours after the last dose of chemotherapy and continuing until 72 hours before the start of the next cycle of chemotherapy. A bone marrow sample taken on day 237 of treatment, after completing consolidation chemotherapy, confirmed that the patient remained in morphologic remission. Due to the aggressive nature of FLT3 mutated AML, the patient continued to receive single agent crenolanib besylate therapy at 100 mg three times daily for 12 months, known as maintenance. Bone marrow samples were obtained sequentially throughout maintenance to monitor the patient's disease and confirm the patient remained in remission. A final bone marrow sample, obtained at the completion of maintenance therapy (day 406 of treatment), confirmed that the patient remained in morphologic remission.

Longitudinal bone marrow samples obtained throughout the course of treatment were analyzed using single cell sequencing. These samples included a baseline sample (Induction D1), a sample obtained at the completion of induction combination therapy (Induction D35), a sample obtained at the completion of consolidation combination therapy (Consolidation D237), a sample obtained approximately one quarter of the way through single agent crenolanib besylate maintenance therapy (Maintenance D294), and a final sample obtained at the completion of single agent crenolanib besylate maintenance therapy (Maintenance D406). Table 1 outlines the samples obtained, the number of cells sequencing, and the number of reads per sample, and the allele drop-out rate for each sample.

TABLE 1—is a sequencing run summary using single-cell DNA (scDNA) analysis via the TAPESTRI platform (Mission Bio, USA). Bone marrow samples of a newly-diagnosed patient with FLT3-AML were collected longitudinally and retrospectively analyzed by since cell genomic sequencing. Tagged cells of all bone marrow analytes equated to a cumulative total of 12,699 cells, with the single-cell DNA library and sequencing method to analyze each individual cell. The average reads over all samples were 17.6M, with an average of 99 reads per amplicon. Number of reads allowed for a high panel uniformity [92-94%]; and, on average, had demonstrated a low allele dropout rate. Cell encapsulation, targeted PCR, and next generation library preparation were performed per the manufacturer's instructions using the TAPESTRI instrument and the Thermo Fisher SimpliAmp thermal cycler (cat #A24811, or equivalent). Sequencing the prepared single-cell DNA library was performed using Illumina's MiSeq instrument, per the manufacturer's instructions. Analysis of next-generation sequencing data was performed by first processing the sequencing data using the TAPESTRI Pipeline to ultimately generate variant calls. The resultant loom files are then imported into the TAPESTRI™ bioinformatics software, Insight, which is used to identify relevant variants to FLT3-AML, including co-occurring and rare mutations.

TABLE 1

Single-cell Sequencing Summary Data from a Newly Diagnosed FLT3-AML Patient's Bone Marrow Samples.

| Sample ID | Number of cells | Number of reads | Reads per cell per Amplicon | Panel Uniformity | ADO |
|---|---|---|---|---|---|
| Induction (D1) | 2,920 | 18.9M | 92 | 94% | 10.28% |
| Induction (D53) | 387 | 14.2M | 599 | 92% | NA |
| Consolidation (D237) | 3,457 | 26.9M | 99 | 96% | 11.31% |
| Maintenance (D294) | 4,583 | 14.6M | 42 | 94% | 5.99% |
| Maintenance (D406) | 1,352 | 13.3M | 106 | 94% | 13.18% |
| Total/Average | 12,699 | 17.6M | 99 | 94% | 8.16% |

*ADO, allele dropout rate

*ADO, allele dropout rate

Single cell sequencing revealed a number of genetic mutations that were not visible using bulk sequencing techniques, including FLT3-D835E, FLT3-D839G, KRAS-G12D, NRAS-G13V, and two separate DNMT3A mutations, R882C and R882H (only the DNMT3A-R882C mutations was visible using bulk sequencing). Single cell sequencing also confirmed the presence of the FLT3-ITD, FLT3-A680V, FLT3-N814K, and NPM1 mutations. Table 2 details the mutations found in the diagnosis (Induction D1) sample.

TABLE 2 is a single-cell sequencing summary of FLT3 variants, FLT3 activating mutations, and co-occurring mutations of a patient with newly diagnosed FLT3-AML variant calls using TAPESTRI pipeline from next-generation (Miseq) sequencing of single-cell DNA library. Analysis shows the variant gene family, nucleotide alteration observed, encoded protein mutated within the gene family, and impact on the transcriptional code of the protein. Furthermore, deleterious annotation of genetic variants using neural networks (DANN) indicates likelihood of a true positive, with a maximum score of 1 [range: 0-1]. Clinical implication for each mutation were pathogenic in nature, despite limitations in scope with MissionBio Insight software providing no coding for clinical implication for A6580V and FLT3-ITD. Each variant subclone also had a percentage genotyped from the total cells analyzed. [range: 66% to 99%] dependent on the variant.

TABLE 2

Single-cell Sequencing Summary of detected FLT3 Variants, FLT3 activating Mutations, and Co-occurring Mutations of a Patient with Newly Diagnosed FLT3-AML.

| Variant | Variation | Protein | Impact | DANN | Clinical Implication | % Cells GT |
|---|---|---|---|---|---|---|
| FLT3 | G/A | A680V | Missense | 1.00 | — | 97% |
| FLT3 | G/T | N841K | Missense | 1.00 | Likely pathogenic | 99% |
| FLT3 | A/C | D835E | Missense | 0.99 | Pathogenic | 99% |
| FLT3 | T/C | D839G | Missense | 1.00 | Likely pathogenic | 99% |
| FLT3 | | ITD 24-30 ins | In frame | N/A | N/A | 92% |
| KRAS | C/T | G12D | Missense | 1.00 | Pathogenic | 94% |
| NRAS | C/A | G13V | Missense | 1.00 | Pathogenic | 90% |
| DNMT3A | G/A | R882C | Missense | 1.00 | Pathogenic | 80% |
| NPM1 | C/CTCTG | insTCTG | Frameshift | N/A | Pathogenic | 66% |

The longitudinal bone marrow samples obtained allowed for the tracking of the above identified mutations over the course of the patient's treatment. Table 3 below demonstrates the loss of several of these mutations after induction and consolidation chemotherapy. After the completion of consolidation, the FLT3-A680V, FLT3-D839G, KRAS-G12D, DNMT3A-R882C, and DNMT3A-R882H mutations remained. The DNMT3A mutations are associated with age and are not necessarily an indicator of potential relapse at the low mutational burdens seen here. It is known that these mutations may persist after treatment. The persistence of the FLT3 and KRAS mutations put the patient at risk of relapse, and their presence after completion of induction and four cycles of consolidation chemotherapy is of concern. However, after approximately two months of single agent crenolanib besylate maintenance therapy, the remaining FLT3 and KRAS mutations were cleared. These mutations remained absent at the completion of maintenance therapy, confirming the benefit of crenolanib besylate singe agent maintenance therapy in suppressing variant FLT3 mutations that may cause relapse.

TABLE 3 is a single-cell DNA analysis that revealed 4 distinct FLT3 subclones at diagnosis, including a FLT3-ITD and three FLT3 activating mutations (D839G, A680V, N841K), with co-occurring NPM1 and two DNMT3A mutations (R882C, R882H). Leukemic clones with either NRAS or KRAS activating mutations, exclusive from FLT3 mutant clones. After the first cycle of induction, single-cell sequencing revealed low level detection of FLT3-ITD (3%), FLT3-D839G (3%) and FLT3-D835E (1%). Analysis of single-cell DNA following consolidation revealed clearance of NPM1 and FLT3-ITD but showed low-level detection of variant FLT3-D839G (1%) and FLT3-A680V (1%) clones. The patient received one-year of crenolanib maintenance, and by day 79 into maintenance, all variant FLT3 clones had also cleared.

TABLE 3

Single-cell Sequencing Data of Variant Allele Frequencies of FLT3 Variants, FLT3 Activating Mutations, and Co-Occurring Mutations in a Newly Diagnosed FLT3-AML Patient's Longitudinal Bone Marrow Samples.

| Variant | Induction (D1) | Induction (D53) | Consolidation (D237) | Maintenance (D294) | Maintenance (D406) |
| --- | --- | --- | --- | --- | --- |
| FLT3 A680V | 20% | 0% | 1% | 0% | 0% |
| FLT3 N841K | 18% | 0% | 0% | 0% | 0% |
| FLT3 D835E | 0% | 1% | 0% | 0% | 0% |
| FLT3 D839G | 1% | 3% | 1% | 0% | 0% |
| FLT3 ITD | 22% | 3% | 0% | 0% | 0% |
| KRAS G12D | 1% | 0% | 1% | 0% | 0% |
| NRAS G13V | 1% | 0% | 0% | 0% | 0% |
| DNMT3A R882C | 41% | 0% | 5% | 6% | 8% |
| DNMT3A R882H | 1% | 3% | 1% | 0% | 0% |
| NPM1 dupTCTG | 44% | 4% | 0% | 0% | 0% |
| Cells Counted | 2920 | 387 | 3457 | 4583 | 1352 |

The results displayed in a tabular format are represented graphically in FIG. 1 below. The co-occurrence of the identified mutations within cells is also displayed. Each vertical bar represents the entire population of bone marrow cells tested in the sample identified at the bottom of the bar. Each population of bone marrow cells bearing a certain set of mutations has been assigned a pattern, as shown in the legend to the right. The relative size of each pattern within the bar is the relative proportion of each distinct population, or clone. The sample obtained at diagnosis shows the greatest clonal heterogeneity. After induction chemotherapy, many of the clonal populations have been cleared. Finally, after maintenance therapy, only wildtype cells, and clones bearing only the DNMT3A-R882C mutation remain. It is important to note that in this representation of the data, small clonal populations corresponding to the persistent FLT3-A680V, FL3-D839G, KRAS-G12D, and DNMT3A-R882H in 1% of cells are not shown due to the limitations of the format.

FIG. 1 shows a graphical Interpretation of Single-cell Sequencing Data of Variant Allele Frequencies of FLT3 Variants, FLT3 Activating Mutations, and Co-Occurring Mutations in a Newly Diagnosed FLT3-AML Patient's Longitudinal Bone Marrow Samples.

Figure 2B:
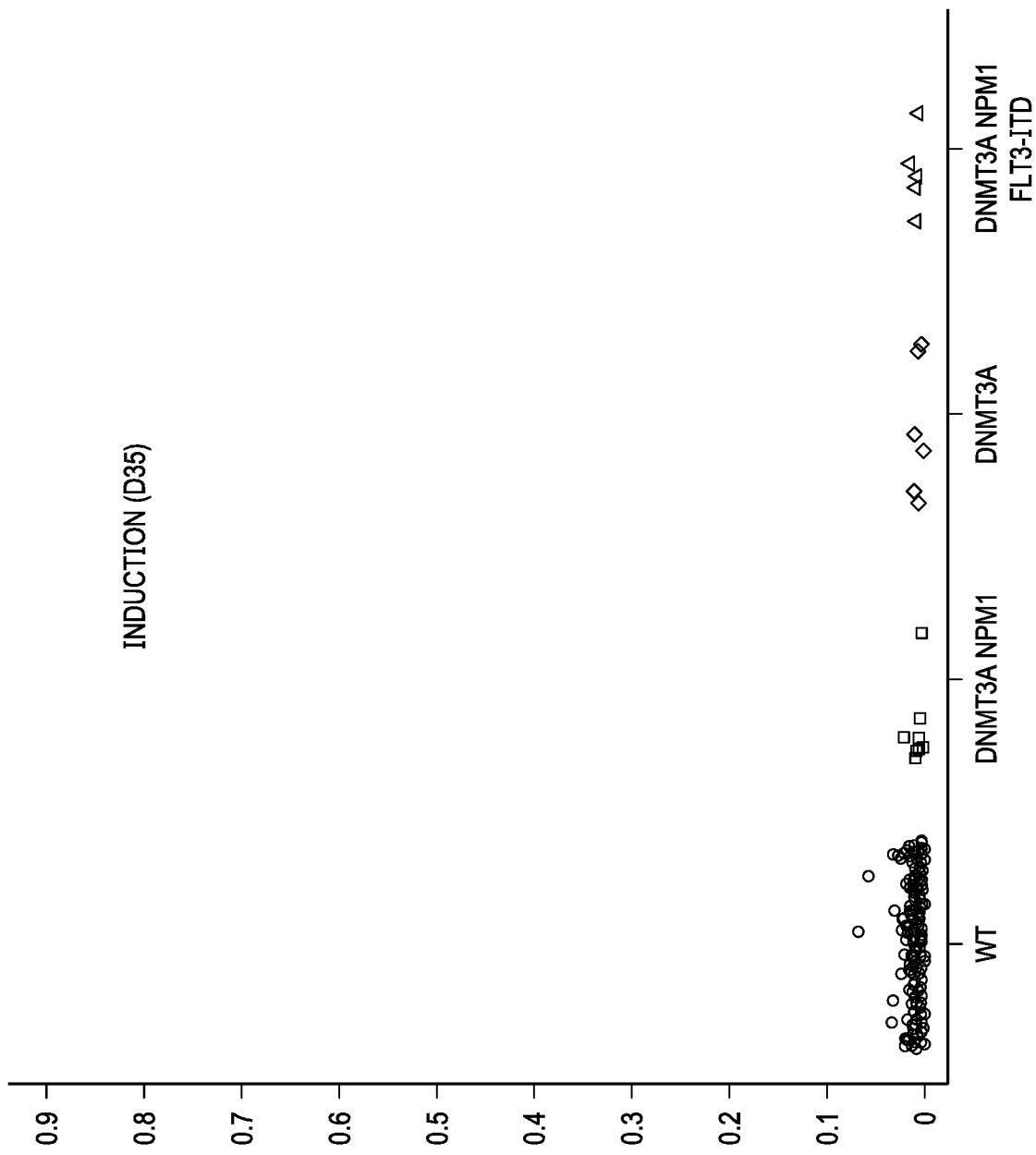

FIGS. 2A and 2B are scatter plots showing individual cells expressing mutant KRAS (y-axis) within bone marrow samples of a patient at diagnosis (FIG. 2A) and 35 days following the start of induction (FIG. 2B). FIG. 2A shows that the cell populations contain the following mutations from left to right; DNMT3A/NPM1/FLT3-A680V/FLT3-ITD, DNMT3A/NPM1/FLT3-N841K, wild type, DNMT3A/NPM1/FLT3-A680V, DNMT3A/NPM1/FLT3-D839G and lastly small subclonal cells with various mutations. FIG. 2B shows that the cell populations are as follows: wild type, DNMT3A/NPM1, DNMT3A, and DNMT3A/NPM1/FLT3-ITD. Treatment with crenolanib eliminated the vast majority of the mutant containing cancer cell populations.

FIGS. 3A and 3B are scatter plots showing individual cells expressing mutant DNMT3 (y-axis) within bone marrow samples of a patient at diagnosis (FIG. 3A) and 35 days following the start of induction (FIG. 3B). FIG. 3A shows that the cell populations contain the following mutations from left to right; DNMT3A/NPM1/FLT3-A680V/FLT3-ITD, DNMT3A/NPM1/FLT3-N841K, wild type, DNMT3A/NPM1/FLT3-A680V, and DNMT3A/NPM1/FLT3-D839G. FIG. 3B shows that the cell populations are as follows: wild type, DNMT3A/NPM1, DNMT3A, DNMT3A/NPM1/FLT3-ITD, and FLT3-D835E. Treatment with crenolanib eliminated the vast majority of the mutant containing cancer cell populations.

FIGS. 4A and 4B are scatter plots showing individual cells expressing mutant NPM1 (y-axis) within bone marrow samples of a patient at diagnosis (FIG. 4A) and 35 days following the start of induction (FIG. 4B). FIG. 4A shows that the cell populations contain the following mutations from left to right; DNMT3A/NPM1/FLT3-A680V/FLT3-ITD, DNMT3A/NPM1/FLT3-N841K, wild type, DNMT3A/NPM1/FLT3-A680V, and DNMT3A/NPM1/FLT3-D839G, and lastly small subclonal cells with various mutations. FIG. 4B shows that the cell populations are as follows: wild type, DNMT3A/NPM1, DNMT3A, DNMT3A/NPM1/FLT3-ITD, and FLT3-D835E. Treatment with crenolanib eliminated the vast majority of the mutant containing cancer cell populations.

Figure 5:
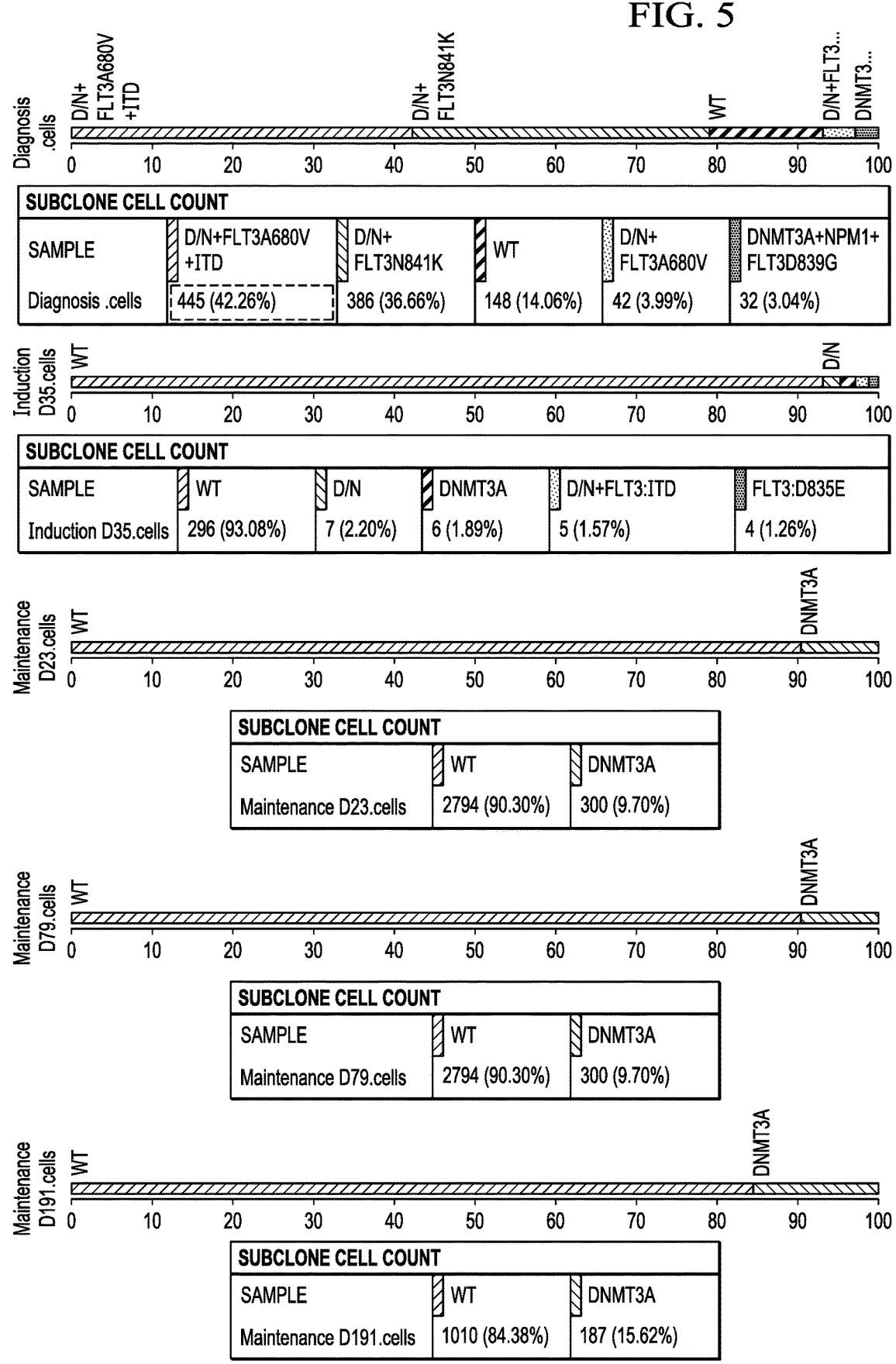
FIG. 5 shows individual plots of the longitudinal bone marrow samples of a patient. Normal wild-type (WT) cells are displayed in grey. The illustration represents total subclonal populations within samples at diagnosis, 35 days following the start of induction, and three timepoints during maintenance. Samples indicate that variant FLT3 and FLT3 activating mutations were eliminated with combination therapy of intensive induction chemotherapy in addition with crenolanib, high-dose cytarabine (HiDAC) consolidation with crenolanib, and single agent crenolanib maintenance for mutational clearance.

FIG. 5 shows individual plots of the longitudinal bone marrow samples of a patient. Normal wild-type (WT) cells are displayed. The illustration represents total sub-clonal populations within samples at diagnosis, 35 days following the start of induction, and three timepoints during maintenance. Samples indicate that variant FLT3 and FLT3 activating mutations were eliminated with combination therapy of intensive induction chemotherapy in addition with crenolanib, high-dose cytarabine (HiDAC) consolidation with crenolanib, and single agent crenolanib maintenance for mutational clearance.

Example 2

A 68-year-old male was diagnosed with AML in 2016. At diagnosis, molecular testing using bulk DNA sequencing methods revealed the patient had wildtype FLT3, and carried mutations in the BCOR, NRAS, and U2AF1 genes, which were considered to be pathological alterations. Initially, the patient was treated with a standard cytarabine/anthracycline based chemotherapy regimen. The patient did not respond to initial treatment and was considered refractory. To treat this patient's disease and overcome the rise in FLT3 ligand that has been documented to occur after successive rounds of chemotherapy, even in FLT3-wildtype patients, this patient was provided oral crenolanib besylate in combination with salvage chemotherapy for relapsed/refractory patients. At baseline, this patient presented with 17% bone marrow blasts. The patient was treated with salvage chemotherapy, comprised of five days of fludarabine, five days of cytarabine, 3 days of idarubicin, and G-CSF, followed by 100 mg of crenolanib besylate three times daily starting on day 7 of treatment.

A bone marrow biopsy taken on day 32 of treatment revealed the patient's bone marrow blasts had been reduced to less than 5% and the patient was determined to have achieved a complete morphological remission in response to crenolanib combination therapy. At this time, the mutations in BCOR, NRAS, and U2AF1 present at diagnosis and study enrollment were not detected using bulk DNA sequencing methods.

The study was designed to determine the safety of crenolanib when combined with standard salvage chemotherapy in patients with relapsed/refractory AML, patients only remained on study for 1-2 cycles of induction crenolanib combination therapy. As this patient achieved a morphologic remission after a single cycle, the patient completed study treatment as per protocol and remains alive and in remission at last follow up. This example illustrates the ability of crenolanib combination therapy to eliminate malignant leukemic cells in a FLT3-wildtype relapsed/refractory AML patient.

Example 3

A 36-year-old male was diagnosed with AML in 2016. At diagnosis, molecular testing using bulk DNA sequencing methods revealed the patient had FLT3-ITD, NRAS, and NPM1 mutations. To treat this patient's disease and overcome the FLT3 mutation, this patient was provided oral crenolanib besylate in combination with standard chemotherapy on a clinical trial for newly diagnosed AML patients with activating FLT3 mutations. At baseline this patient presented with 8% bone marrow blasts. The patient was treated with induction chemotherapy, comprised of seven days of cytarabine and three days of daunorubicin, followed by 100 mg of crenolanib besylate three times daily starting on day 10 of treatment.

A bone marrow biopsy taken on day 24 of treatment revealed the patient's bone marrow blasts had been reduced to 5% and the patient was determined to have achieved a complete morphologic remission in response to crenolanib combination therapy. At this time, the FLT3-ITD mutation present at diagnosis was no longer detected using a PCR based test (the other mutations present at diagnosis were not tested at this time). In an effort to maintain remission, the patient was then administered one cycle of high dose cytarabine consolidation chemotherapy, followed by oral crenolanib besylate at 100 mg three times daily starting 48 hours after the last dose of chemotherapy. A bone marrow sample taken on day 98 of treatment, after completing one cycle of consolidation therapy, confirmed that the patient remained in remission, and the FLT3-ITD mutation present at diagnosis remained undetectable by standard PCR tests. This example illustrates the ability of crenolanib combination therapy to clear malignant leukemic cells and a FLT3-ITD mutation from a newly diagnosed AML patient.

Example 4

A 59-year-old male was diagnosed with AML in 2017. At diagnosis, molecular testing using bulk DNA sequencing methods revealed the patient had FLT3-D835V, FLT3-D835E, DNMT3A, NRAS, RUNX1, BCOR, and U2AF1 mutations. To treat this patient's disease and overcome the FLT3 mutations, this patient was provided oral crenolanib besylate in combination with standard chemotherapy on a clinical trial for newly diagnosed AML patients with activating FLT3 mutations. At baseline this patient presented with 70% bone marrow blasts. The patient was treated with two cycles of induction chemotherapy, comprised of seven days of cytarabine and three days of idarubicin, followed by 100 mg of crenolanib besylate three times daily starting on day 10 of treatment.

A bone marrow biopsy taken on day 50 of treatment revealed the patient's bone marrow blasts had been reduced to less than 5%, and the patient was determined to have achieved a complete morphologic remission in response to crenolanib combination therapy. At this time, the FLT3 mutations (D835V and D835E) present at diagnosis were not detected using bulk NGS methods. This example illustrates the ability of crenolanib combination therapy to clear malignant leukemic cells and multiple FLT3 mutations from a newly diagnosed AML patient.

Example 5

A 36-year-old female was diagnosed with AML in 2012. At diagnosis, molecular testing revealed the patient had a FLT3-D835 mutation. Initially, the patient was treated with standard induction chemotherapy and a bone marrow transplant. Unfortunately, the patient subsequently relapsed and was treated with salvage chemotherapy, achieving a brief remission before relapsing again. At second relapse, the patient was found to still have a FLT3-D835 mutation, as well as mutations in the NPM1, NOTCH1, CEBPA, and WT1 genes. To treat this patient's disease and overcome the FLT3-D835 mutation, this patient was provided oral crenolanib besylate on a clinical trial for relapsed/refractory AML patients with activating FLT3 mutations. At baseline this patient presented with 90% bone marrow blasts. The patient was treated with single agent crenolanib besylate at a dose of 200 mg/m$^2$ three times daily.

A bone marrow biopsy taken on day 53 of treatment revealed the patient's bone marrow blasts had been reduced to less than 5%, and the patient was determined to have achieved a complete morphologic remission (with incomplete hematological recovery) in response to crenolanib single agent therapy. At this time, the FLT3-D835 mutation present at diagnoses was not detected using PCR based techniques. The example illustrates the ability of single agent crenolanib therapy to clear malignant leukemic blasts and a FLT3-D835 mutation in a heavily pretreated relapsed/refractory AML patient.

Example 6

An 87-year-old female was diagnosed with AML in 2014. At diagnosis, molecular testing revealed the patient had a FLT3-ITD mutation. Initially, the patient was treated with low-dose standard induction chemotherapy followed by sorafenib maintenance; however, the patient did not achieve a complete morphologic remission and within 5 months the patient was considered to have progressive disease. Molecular testing performed after sorafenib treatment revealed the patient had acquired a FLT3-D835 mutation and a second FLT3-ITD mutation. In addition, bulk DNA sequencing found mutations in the NRAS and RUNX1 genes. To treat this patient's disease and overcome the FLT3-ITD and FLT3-D835 mutations, this patient was provided oral crenolanib besylate on a clinical trial for relapsed/refractory AML patients with activating FLT3 mutations. At baseline, this patient presented with 68% bone marrow blasts. The patient was treated with single agent crenolanib besylate at a dose of 200 mg/m$^2$ three times daily.

A bone marrow biopsy taken on day 27 of treatment revealed the patient's bone marrow blasts had been reduced to 7%, and the patient was determined to have achieved a partial morphologic remission in response to crenolanib single agent therapy. At this time, the allelic ratio of the one of the FLT3-ITD mutations had been reduced by 75%, and the second ITD mutation was not detectable. This example illustrates the ability of single agent crenolanib to significantly reduce malignant leukemic blasts and reduce the mutation burden of multiple FLT3 mutations in a relapsed/refractory patient.

Example 7

A 54-year-old female was diagnosed with AML in 2016. Her diagnostic bone marrow aspirate was sent for NGS of cancer associated genes. She was found to have FLT3-ITD, FLT3-I836del, FLT3-N841I, FLT3-V491L, FLT3-V592A, IDH2, NMP1, and SRSF2 mutations. To treat this patient's disease and overcome the FLT3 mutations, this patient was provided oral crenolanib besylate in combination with standard chemotherapy on a clinical trial for newly diagnosed AML patients with activating FLT3 mutations. At baseline this patient presented with 95% bone marrow blasts. The patient was treated with induction chemotherapy, comprised of seven days of cytarabine and three days of idarubicin, followed by 100 mg of crenolanib besylate three times daily starting on day 10 of treatment.

A bone marrow biopsy taken on day 27 of treatment revealed the patient's bone marrow blasts had been reduced to 2% and the patient was determined to have achieved a complete morphologic remission in response to crenolanib combination therapy. At this time molecular testing could not find the FLT3-ITD nor the FLT3-I836del; the other mutations were not tested for. In an effort to maintain remission, the patient was then administered four cycles of high dose cytarabine consolidation chemotherapy. In each cycle, the patient received cytarabine chemotherapy at standard doses, followed by oral crenolanib besylate at 100 mg three times daily starting 48 hours after the last dose of chemotherapy and continuing until 72 hours before the start of the next cycle of chemotherapy. Due to the aggressive nature of FLT3 mutated AML, the patient continued to receive single agent crenolanib besylate therapy at 100 mg three times daily for 21 months, known as maintenance.

Example 8

A one-year old boy was diagnosed with t(9; 11)+AML in April of 2016. He underwent two cycles cytarabine, daunorubicin, etoposide (ADE), followed by one cycle each of cytarabine etoposide (AE) and mitoxantrone cytarabine (MA) and went into remission for two years. In late 2018 the patient relapsed with leukemia and had extramedullary disease in the sinuses, orbits, and sphenoids. The patient then received one cycle of fludarabine, cytarabine, and G-CSF (FLAG), but had no response. The patient again received FLAG with the addition of gemtuzumab ozogamicin and azacytidine and was able to achieve a remission that was negative by flow cytometry for measurable residual disease and then underwent an allogeneic stem cell transplant with umbilical cord stem cells. The patient then experienced a second relapse in 2019 at which point the patient was found by bulk DNA sequencing to have a FLT3-A848P mutation. This patient was then enrolled on a clinical trial and received one cycle of venetoclax with high dose cytarabine and idarubicin, but had no response to treatment. This patient then received three doses of liposomal chemotherapy (daunorubicin and cytarabine (VYXEOS®) and gemtuzumab ozogamicin; five days later began taking 66.7 mg/m² crenolanib besylate orally. One month later he was found to be in complete morphologic remission without count recovery. The patient stayed on crenolanib until one week prior to another allogeneic stem cell transplant. The patient is now more than 100 days post-transplant and is still in remission.

The present invention includes a method of treating a subject with a proliferative disorder comprising a wild type FLT3 with or without one or more co-occurring FLT3 mutations, the method comprising, consisting essentially of, or consisting of: administering to the subject a therapeutically effective amount of crenolanib or a pharmaceutically acceptable salt thereof in combination with at least one of an alkylating agent, an antimetabolite, a natural product or a combination thereof. In another aspect a method of treating a subject with a proliferative disorder comprising a wild type FLT3 one or more co-occurring RAS mutations, the method comprising of administering to the subject a therapeutically effective amount of crenolanib or a pharmaceutically acceptable salt thereof in combination with at least one of an alkylating agent, an antimetabolite, a natural product or a combination thereof. In yet another aspect is a method of preventing a relapse of a proliferative disorder; comprising administering a therapeutically effective amount of crenolanib or a pharmaceutically acceptable salt thereof and as a single agent or in combination with another pharmaceutical agent. In one aspect where the proliferative disorder is characterized by comprising one or more function altering mutations and at least one recurrent genetic mutation. In one aspect, the minimal residual disease is detected by: obtaining a sample from the subject; single cell sequencing the genetic code of the abovementioned genes, wherein the sequencing comprises at least 1,000,000 reads/sample; and analyzing only samples were there is allele dropout rate of 10% or less. In another aspect, the presence or absence of one or more mutations is found in the abovementioned genes which create patient-specific single cell mutations profiles correlating with the proliferative disorder. In another aspect, the abovementioned recurrent genetic mutations are found in at least one of FLT3, NPM1, DNMT3A, NRAS, KRAS, JAK2, PTPN11, TET2, IDH1, IDH2, WT1, RUNX1, CEBPA, ASXL1, BCOR, SF3B1, U2AF1, STAG2, SETBP1, ZRSR2, GRB7, SRSF2, MLL, NUP98, ETV6, TCL1A, TUSC3, BRP1, CD36, TYK2, TP53, EZH2, GATA2, KIT, PHF6, MYC, ERG, MYD88, RAD21, STAT3, NF1, BRAF, KDM6A, SETBP1, CALR, CBL, KMT2A, PHF6, SMC1A, CHEK2, GNAS, PPM1D, SMC3, ZRSR2, CSF3R, HRAS, MPL, PTEN, ATM, MUTYH, or others. In another aspect, the FLT3 mutations found include at least one of FLT3-ITD, FLT3-TKD, or other FLT3 mutation variants. In another aspect, the FLT3-TKD mutations include a point mutation resulting in an alteration or deletion in at least one F612, L616, K663, M664, M665, N676, A680, F691, A833, R834, D835, I836, D839, N841, Y842, or A848. In another aspect, the FLT3 variant mutations include a point mutations resulting in an alteration or deletion in at least one of L20, D324, K429, L442, E444, S451, V491, Y572, E573, L576, Y572, Y572, Q580, V591, T582, D586, Y589, V592, F594, E596, E598, Y599, D600, R607, A848 or others. In another aspect, the subject is a pediatric subject.

In another aspect, further comprising the steps of: repeating the steps (a) through (c) from one or more longitudinally successive samples from the subject, combining one or more longitudinal single cell genomic mutational profiles to determine the presence or absence of one or more mutations that changes as a response to administering a therapeutically effective amount of crenolanib or a pharmaceutically acceptable salt thereof and determining measurable residual disease status of said proliferative disorder from an increase or decrease of percentage of patient-specific singe cell mutational profiles after treatment that is correlated with said proliferative disorder. In another aspect, the sample obtained is at least one of bone marrow, peripheral blood, or tumor tissue. In another aspect, the single cell sequencing is comprised of using TAPESTRI™ platform to prepare genomic DNA for the abovementioned genes with markers that are associated per cell, and sequencing said prepared DNA with at least one of MiSeq, HiSeq, or NovaSeq sequencing platforms. In another aspect, the subject is a pediatric subject.

In another embodiment, the present invention includes a method of treating a subject with a proliferative disorder that comprises a wild type FLT3 with one or more co-occurring RAS mutations, the method comprising, consisting essentially of, or consisting of: administering to the subject a therapeutically effective amount of crenolanib or a pharmaceutically acceptable salt thereof in combination with at least one of alkylating agents, antimetabolite, natural product, or a combination thereof. In one aspect, a minimal residual disease of the proliferative disorder is detected by: (a) obtaining a sample from the subject comprising neoplastic cells; (b) single cell sequencing the sample wherein the sequencing comprises at least 1,000,000 reads/sample; and (c) analyzing the mutations from only samples with an allele dropout rate of 10% or less. In another aspect, a presence or absence of the one or more mutations is used to make a patient-specific single cell mutational profiles correlating with the proliferative disorder. In another aspect, the RAS mutation is at least one of an NRAS or a KRAS mutation. In another aspect, the one or more co-occurring mutations are at least one of FLT3, NPM1, DNMT3A, JAK2, PTPN11, TET2, IDH1, IDH2, WT1, RUNX1, CEBPA, ASXL1, BCOR, SF3B1, U2AF1, STAG2, SETBP1, ZRSR2, GRB7, SRSF2, MLL, NUP98, ETV6, TCL1A, TUSC3, BRP1, CD36, TYK2, TP53, EZH2, GATA2, KIT, PHF6, MYC, ERG, MYD88, RAD21, STAT3, NF1, BRAF, KDM6A, SETBP1, CALR, CBL, KMT2A, PHF6, SMC1A, CHEK2, GNAS, PPM1D, SMC3, ZRSR2, CSF3R, HRAS, MPL, PTEN, ATM, or MUTYH. In another aspect, method further comprising the steps of: repeating the steps (a) through (c) from one or more longitudinally successive samples from the subject; combining one or more longitudinal single cell genomic mutational profiles to determine a presence or absence of the one or more mutations that change in response to administering a therapeutically effective amount of crenolanib or a pharmaceutically acceptable salt thereof; and determining a measurable residual disease status of the proliferative disorder measured as an increase or decrease of percentage of patient-specific single cell mutational profiles after treatment that are correlated with the proliferative disorder. In another aspect, the sample obtained is at least one of bone marrow, peripheral blood or tumor tissue. In another aspect, the single cell sequencing comprises preparing genomic DNA with one or more markers per cell and sequencing the prepared DNA. In another aspect, the single cell sequencing uses aMiSeq, HiSeq, or NovaSeq platform. In another aspect, the alkylating agent is selected from at least one of: carmustine, chlorambucil, cyclophosphamide, ifosfamide, lomustine, streptozotocin, temozolomide, cisplatin, carboplatin, nedaplatin, or oxaliplatin. In another aspect, the antimetabolite is selected from at least one of: methotrexate, pemetrexed, ralititrexed, cytarabine, fludarabine, fluorouracil, floxuridine, capcitabine, or gemcitabine. In another aspect, the natural product is selected from at least one of: vinblastine, vinorelbine, vincristine, vindesine, vinflunine, paclitaxel, docetaxel, cabazitaxel, etoposide, teniposide, topotecan, irinotecan, daunorubicin, doxorubicin, idarubicin, eiprubicin, valrubicin, mitoxantrone, bleomycin, estramustine, and/or mitomycin. In another aspect, the subject further comprises a mutant FLT3 tyrosine kinase. In another aspect, the subject is a pediatric patient.

In another embodiment, the present invention includes a method of preventing a relapse of a proliferative disorder in a subject previously treated to be free of the proliferative disorder comprising, consisting essentially of, or consisting of: administering to the subject a therapeutically effective amount of crenolanib or a pharmaceutically acceptable salt thereof for a sufficient period of time following a response to induction chemotherapy, consolidation, or following hematopoietic stem cell transplantation to prevent the relapse of the proliferative disorder. In one aspect, the proliferative disorder is characterized by comprising one or more function altering mutations and at least one recurrent genetic mutation. In another aspect, the proliferative disorder is characterized by comprising a wild type FLT3 with or without one or more co-occurring mutations. In another aspect, the subject was previously treated with: an alkylating agent is selected from at least one of: carmustine, chlorambucil, cyclophosphamide, ifosfamide, lomustine, streptozotocin, temozolomide, cisplatin, carboplatin, nedaplatin, or oxaliplatin; an antimetabolite is selected from at least one of: methotrexate, pemetrexed, ralititrexed, cytarabine, fludarabine, fluorouracil, floxuridine, capcitabine, or gemcitabine; or a natural product is selected from at least one of: vinblastine, vinorelbine, vincristine, vindesine, vinflunine, paclitaxel, docetaxel, cabazitaxel, etoposide, teniposide, topotecan, irinotecan, daunorubicin, doxorubicin, idarubicin, eiprubicin, valrubicin, mitoxantrone, bleomycin, estramustine, and/or mitomycin. In another aspect, the one or more co-occurring mutations are at least one of: NPM1, DNMT3A, NRAS, KRAS, JAK2, PTPN11, TET2, IDH1, IDH2, WT1, RUNX1, CEBPA, ASXL1, BCOR, SF3B1, U2AF1, STAG2, SETBP1, ZRSR2, GRB7, SRSF2, MLL, NUP98, ETV6, TCL1A, TUSC3, BRP1, CD36, TYK2, TP53, EZH2, GATA2, KIT, PHF6, MYC, ERG, MYD88, RAD21, STAT3, NF1, BRAF, KDM6A, SETBP1, CALR, CBL, KMT2A, PHF6, SMC1A, CHEK2, GNAS, PPM1D, SMC3, ZRSR2, CSF3R, HRAS, MPL, PTEN, ATM, or MUTYH. In another aspect, the subject is a pediatric patient.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited features, elements, components, groups, integers, and/or steps, but do not exclude the presence of other unstated features, elements, components, groups, integers and/or steps. In embodiments of any of the compositions and methods provided herein, "comprising" may be replaced with "consisting essentially of" or "consisting of". As used herein, the term "consisting" is used to indicate the presence of the recited integer (e.g., a feature, an element, a characteristic, a property, a method/process step or a limitation) or group of integers (e.g., feature(s), element (s), characteristic(s), property(ies), method/process steps or limitation(s)) only. As used herein, the phrase "consisting essentially of" requires the specified features, elements, components, groups, integers, and/or steps, but do not exclude the presence of other unstated features, elements, components, groups, integers and/or steps as well as those that do not materially affect the basic and novel characteristic(s) and/or function of the claimed invention.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

Anderson, P. O., Knoben, J. E., & Troutman, W. G. (2002). Handbook of clinical drug data (10th ed.). New York; Toronto: McGraw-Hill Medical Pub. Division.

Daver, N., Schlenk, R. F., Russell, N. H., & Levis, M. J. (2019). Targeting FLT3 mutations in AML: review of current knowledge and evidence. Leukemia. doi:10.1038/s41375-018-0357-9

Ding, L., et al. (2012). Clonal evolution in relapsed acute myeloid leukaemia revealed by whole-genome sequencing. Nature, 481(7382), 506-510. doi:10.1038/nature10738

Eastburn, D. J., et al. (2017). High-Throughput Single-Cell DNA Sequencing of AML Tumors with Droplet Microfluidics. Blood, 130(Suppl 1), 3965-3965.

Goldstein, A., Pratt, W. B., & Taylor, P. (1990). Principles of drug action: the basis of pharmacology (3rd ed.). New York: Churchill Livingstone.

Goodman, L. S., Hardman, J. G., Limbird, L. E., & Gilman, A. G. (2001). Goodman and Gilman's the pharmacological basis of therapeutics (10th ed.). New York: McGraw-Hill.

Katzung, B. G. (2004). Basic & clinical pharmacology (9th ed.). New York: Lange Medical Books/McGraw Hill.

Martindale, W., Reynolds, J. E. F., & Royal Pharmaceutical Society of Great Britain. Council. (1996). The extra pharmacopoeia (31st ed.). London: Royal Pharmaceutical Society.

Ommen, H. B. (2016). Monitoring minimal residual disease in acute myeloid leukaemia: a review of the current evolving strategies. Ther Adv Hematol, 7(1), 3-16. doi: 10.1177/2040620715614529

Papaemmanuil, E., et al. (2016). Genomic Classification and Prognosis in Acute Myeloid Leukemia. N Engl J Med, 374(23), 2209-2221. doi:10.1056/NEJMoa1516192

Remington, J. P., & Gennaro, A. R. (2000). Remington: the science and practice of pharmacy (20th ed ed.). Baltimore, Md.: Lippincott Williams & Wilkins.

Tyner, J. W., et al. (2018). Functional genomic landscape of acute myeloid leukaemia. Nature. doi:10.1038/s41586-018-0623-z van Galen, P., et al. (2019). Single-Cell RNA-Seq Reveals AML Hierarchies Relevant to Disease Progression and Immunity. Cell, 176(6), 1265-1281 e1224. doi:10.1016/j.cell.2019.01.031

Wilkes, G. M. (2016). Oncology Nursing Drug Handbook 2016 (20 ed.). Sudbury: Jones & Bartlett Publishers.

What is claimed is:

1. A method of treating a subject with a mutation that causes a proliferative disorder, with or without a mutant FLT3 tyrosine kinase, the method comprising administering to the subject a therapeutically effective amount of crenolanib or a pharmaceutically acceptable salt thereof in combination with at least one of an alkylating agent, an antimetabolite, a natural product, or a combination thereof, wherein:
a minimal residual disease of the proliferative disorder is detected by:
a. obtaining a sample from the subject comprising neoplastic cells;
b. single cell sequencing the sample wherein the sequencing comprises at least 1,000,000 reads/sample; and
c. analyzing the mutations from only samples with an allele dropout rate of 10% or less; and
further comprising the steps of:
repeating the steps (a) through (c) from one or more longitudinally successive samples from the subject;
combining one or more longitudinal single cell genomic mutational profiles to determine a presence or absence of the one or more co-occurring mutations that change in response to administration of the therapeutically effective amount of crenolanib or a pharmaceutically acceptable salt thereof;
determining the measurable residual disease status of the proliferative disorder measured as an increase or decrease of a percentage of patient-specific single cell mutational profiles after treatment that are correlated with the proliferative disorder; and
treating the subject with an increase in the measurable residual disease in the therapeutically effective amount of crenolanib or a pharmaceutically acceptable salt thereof in combination with at least one of the alkylating agent, antimetabolite, natural product, or combination thereof.

2. The method of claim 1, wherein a presence or absence of the one or more mutations is used to make a patient-specific single cell mutational profiles correlating with the proliferative disorder.

3. The method of claim 1, wherein the one or more co-occurring mutations are at least one of: NPM1, DNMT3A, NRAS, KRAS, JAK2, PTPN11, TET2, IDH1, IDH2, WT1, RUNX1, CEBPA, ASXL1, BCOR, SF3B1, U2AF1, STAG2, SETBP1, ZRSR2, GRB7, SRSF2, MLL, NUP98, ETV6, TCL1A, TUSC3, BRP1, CD36, TYK2, TP53, EZH2, GATA2, KIT, PHF6, MYC, ERG, MYD88, RAD21, STATS, NF1, BRAF, KDM6A, SETBP1, CALR, CBL, KMT2A, PHF6, SMC1A, CHEK2, GNAS, PPM1D, SMC3, ZRSR2, CSF3R, HRAS, MPL, PTEN, ATM, or MUTYH.

4. The method of claim 1, wherein the FLT3 mutation is at least one of: FLT3-ITD, FLT3-TKD, or other FLT3 mutation variants.

5. The method of claim 4, wherein the FLT3-TKD mutation is an alteration, a deletion, or a point mutation in at least one F612, L616, M664, M665, N676, A680, F691, D835, I836, D839, N841, Y842, or A848.

6. The method of claim 4, wherein the FLT3 mutation include point mutations resulting in an alteration or deletion in at least one of L20, D324, L442, E444, S451, V491, Y572, E573, L576, Y572, Q580, V591, T582, D586, Y589, V592, F594, E596, E598, Y599, D600, R607, or A848.

7. The method of claim 1, wherein the sample obtained is at least one of bone marrow, peripheral blood, or tumor tissue.

8. The method of claim 1, wherein the single cell sequencing comprises preparing genomic DNA with one or more markers per cell and sequencing the prepared DNA.

9. The method of claim 1, wherein the single cell sequencing uses a MiSeq, HiSeq, or NovaSeq platform.

10. The method of claim 1, wherein the alkylating agent is selected from at least one of: carmustine, chlorambucil, cyclophosphamide, ifosfamide, lomustine, streptozotocin, temozolomide, cisplatin, carboplatin, nedaplatin, or oxaliplatin.

11. The method of claim 1, wherein the antimetabolite is selected from at least one of: methotrexate, pemetrexed, ralititrexed, cytarabine, fludarabine, fluorouracil, floxuridine, capcitabine, or gemcitabine.

12. The method of claim 1, wherein the natural product is selected from at least one of: vinblastine, vinorelbine, vincristine, vindesine, vinflunine, paclitaxel, docetaxel, cabazitaxel, etoposide, teniposide, topotecan, irinotecan, daunorubicin, doxorubicin, idarubicin, eiprubicin, valrubicin, mitoxantrone, bleomycin, estramustine, and/or mitomycin.

13. The method of claim 1, wherein the subject is a pediatric patient.

14. A method of treating a subject with a proliferative disorder that comprises a wild type FLT3 with one or more co-occurring RAS mutations, the method comprising administering to the subject a therapeutically effective amount of crenolanib or a pharmaceutically acceptable salt thereof in combination with at least one of alkylating agent, antimetabolite, natural product, or a combination thereof, wherein
a minimal residual disease of the proliferative disorder is detected by:
a. obtaining a sample from the subject comprising neoplastic cells;
b. single cell sequencing the sample wherein the sequencing comprises at least 1,000,000 reads/sample; and
c. analyzing the mutations from only samples with an allele dropout rate of 10% or less; and
further comprising the steps of:
repeating the steps (a) through (c) from one or more longitudinally successive samples from the subject;
combining one or more longitudinal single cell genomic mutational profiles to determine a presence or absence of the one or more mutations that change in response to administering a therapeutically effective amount of crenolanib or a pharmaceutically acceptable salt thereof;
determining a measurable residual disease status of the proliferative disorder measured as an increase or decrease of a percentage of patient-specific single cell mutational profiles after treatment that are correlate with the proliferative disorder; and
treating the subject with an increase in the measurable residual disease in the therapeutically effective amount of crenolanib or a pharmaceutically acceptable salt thereof in combination with at least one of the alkylating agent, antimetabolite, natural product, or combination thereof.

15. The method of claim 14, wherein a presence or absence of the one or more mutations is used to make a patient-specific single cell mutational profiles correlating with the proliferative disorder.

16. The method of claim 14, wherein the RAS mutation is at least one of an NRAS or a KRAS mutation.

17. The method of claim 14, wherein the one or more co-occurring mutations are at least one of FLT3, NPM1, DNMT3A, JAK2, PTPN11, TET2, IDH1, IDH2, WT1, RUNX1, CEBPA, ASXL1, BCOR, SF3B1, U2AF1, STAG2, SETBP1, ZRSR2, GRB7, SRSF2, MLL, NUP98, ETV6, TCL1A, TUSC3, BRP1, CD36, TYK2, TP53, EZH2, GATA2, KIT, PHF6, MYC, ERG, MYD88, RAD21, STATS, NF1, BRAF, KDM6A, SETBP1, CALR, CBL, KMT2A, PHF6, SMC1A, CHEK2, GNAS, PPM1D, SMC3, ZRSR2, CSF3R, HRAS, MPL, PTEN, ATM, or MUTYH.

18. The method of claim 14, wherein the sample obtained is at least one of bone marrow, peripheral blood or tumor tissue.

19. The method of claim 14, wherein the single cell sequencing comprises preparing genomic DNA with one or more markers per cell and sequencing the prepared DNA.

20. The method of claim 14, wherein the single cell sequencing uses aMiSeq, HiSeq, or NovaSeq platform.

21. The method of claim 14, wherein the alkylating agent is selected from at least one of: carmustine, chlorambucil, cyclophosphamide, ifosfamide, lomustine, streptozotocin, temozolomide, cisplatin, carboplatin, nedaplatin, or oxaliplatin.

22. The method of claim 14, wherein the antimetabolite is selected from at least one of: methotrexate, pemetrexed, ralititrexed, cytarabine, fludarabine, fluorouracil, floxuridine, capcitabine, or gemcitabine.

23. The method of claim 14, wherein the natural product is selected from at least one of: vinblastine, vinorelbine, vincristine, vindesine, vinflunine, paclitaxel, docetaxel, cabazitaxel, etoposide, teniposide, topotecan, irinotecan, daunorubicin, doxorubicin, idarubicin, eiprubicin, valrubicin, mitoxantrone, bleomycin, estramustine, and/or mitomycin.

24. The method of claim 14, wherein the subject further comprises a mutant FLT3 tyrosine kinase.

25. The method of claim 14, wherein the subject is a pediatric patient.

26. A method of preventing a relapse of a proliferative disorder in a subject previously treated to be free of the proliferative disorder and currently in remission comprising administering to the subject a therapeutically effective amount of crenolanib or a pharmaceutically acceptable salt thereof as maintenance treatment for a sufficient period of time following a response to induction chemotherapy, consolidation, or following hematopoietic stem cell transplantation to prevent the relapse of the proliferative disorder, wherein:
the subject is monitored for measurable residual disease by:
a. obtaining a blood or bone marrow sample from the subject
b. single cell sequencing the sample wherein the sequencing comprises at least 1,000,000 reads/sample; and
c. analyzing the sequencing from only samples with an allele dropout rate of 10% or less
further comprising the steps of:
repeating the steps (a) through (c) from one or more longitudinally successive samples from the subject;
combining one or more longitudinal single cell genomic mutational profiles to determine a presence or absence of the one or more mutations that change in response to administering a therapeutically effective amount of crenolanib or a pharmaceutically acceptable salt thereof;
determining a measurable residual disease status of the proliferative disorder measured as an increase or decrease of a percentage of patient-specific single cell mutational profiles after treatment that are correlate with the proliferative disorder; and
treating the subject with an increase in the measurable residual disease in the therapeutically effective amount of crenolanib or a pharmaceutically acceptable salt thereof in combination with at least one of the alkylating agent, antimetabolite, natural product, or combination thereof.

27. The method of claim 26, wherein the proliferative disorder is characterized by comprising one or more function altering mutations and at least one recurrent genetic mutation.

28. The method of claim 26, wherein the proliferative disorder is characterized by comprising a wild type FLT3 with or without one or more co-occurring mutations.

29. The method of claim 26, wherein the subject was previously treated with:
an alkylating agent is selected from at least one of: carmustine, chlorambucil, cyclophosphamide, ifosfamide, lomustine, streptozotocin, temozolomide, cisplatin, carboplatin, nedaplatin, or oxaliplatin;
an antimetabolite is selected from at least one of: methotrexate, pemetrexed, ralititrexed, cytarabine, fludarabine, fluorouracil, floxuridine, capcitabine, or gemcitabine;
or a natural product is selected from at least one of: vinblastine, vinorelbine, vincristine, vindesine, vinflunine, paclitaxel, docetaxel, cabazitaxel, etoposide, teniposide, topotecan, irinotecan, daunorubicin, doxorubicin, idarubicin, eiprubicin, valrubicin, mitoxantrone, bleomycin, estramustine, and/or mitomycin.

30. The method of claim 26, wherein the one or more co-occurring mutations are at least one of: NPM1, DNMT3A, NRAS, KRAS, JAK2, PTPN11, TET2, IDH1, IDH2, WT1, RUNX1, CEBPA, ASXL1, BCOR, SF3B1, U2AF1, STAG2, SETBP1, ZRSR2, GRB7, SRSF2, MLL, NUP98, ETV6, TCL1A, TUSC3, BRP1, CD36, TYK2, TP53, EZH2, GATA2, KIT, PHF6, MYC, ERG, MYD88, RAD21, STATS, NF1, BRAF, KDM6A, SETBP1, CALR, CBL, KMT2A, PHF6, SMC1A, CHEK2, GNAS, PPM1D, SMC3, ZRSR2, CSF3R, HRAS, MPL, PTEN, ATM, or MUTYH.

31. The method of claim 26, wherein the subject is a pediatric patient.

* * * * *